(12) United States Patent
Ji et al.

(10) Patent No.: US 11,414,656 B2
(45) Date of Patent: Aug. 16, 2022

(54) METHODS FOR ENRICHING FOR DUPLEX READS IN SEQUENCING AND ERROR CORRECTION

(71) Applicant: GRAIL, Inc., Menlo Park, CA (US)

(72) Inventors: Lijuan Ji, Santa Clara, CA (US); Nathan Hunkapiller, Belmont, CA (US); Suchitra Ramani, Fremont, CA (US)

(73) Assignee: GRAIL, Inc., Menlo Park, CA (US)

( * ) Notice: Subject to any disclaimer, the term of this patent is extended or adjusted under 35 U.S.C. 154(b) by 722 days.

(21) Appl. No.: 16/221,358

(22) Filed: Dec. 14, 2018

(65) Prior Publication Data

US 2019/0225962 A1    Jul. 25, 2019

Related U.S. Application Data

(60) Provisional application No. 62/599,580, filed on Dec. 15, 2017.

(51) Int. Cl.

| | | |
|---|---|---|
| *C12N 15/10* | (2006.01) | |
| *C12Q 1/6806* | (2018.01) | |
| *C12Q 1/6848* | (2018.01) | |
| *C12Q 1/6855* | (2018.01) | |
| *G16B 30/10* | (2019.01) | |
| *G16B 35/00* | (2019.01) | |
| *C40B 50/04* | (2006.01) | |
| *C40B 50/10* | (2006.01) | |
| *C12N 15/66* | (2006.01) | |
| *C40B 40/06* | (2006.01) | |
| *C40B 80/00* | (2006.01) | |

(52) U.S. Cl.
CPC ..... *C12N 15/1093* (2013.01); *C12N 15/1072* (2013.01); *C12N 15/1089* (2013.01); *C12N 15/66* (2013.01); *C12Q 1/6806* (2013.01); *C12Q 1/6848* (2013.01); *C12Q 1/6855* (2013.01); *G16B 30/10* (2019.02); *G16B 35/00* (2019.02); *C12Y 207/07007* (2013.01); *C40B 40/06* (2013.01); *C40B 50/04* (2013.01); *C40B 50/10* (2013.01); *C40B 80/00* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 6,818,395 B1 | 11/2004 | Quake et al. |
| 7,169,560 B2 | 1/2007 | Lapidus et al. |
| 7,282,337 B1 | 10/2007 | Harris et al. |
| 7,666,593 B2 | 2/2010 | Lapidus |
| 2002/0164629 A1 | 11/2002 | Quake et al. |
| 2009/0026082 A1 | 1/2009 | Rothberg et al. |
| 2009/0127589 A1 | 5/2009 | Rothberg et al. |
| 2009/0156412 A1 | 6/2009 | Harris et al. |
| 2009/0191565 A1 | 7/2009 | Lapidus et al. |
| 2010/0035252 A1 | 2/2010 | Rothberg et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2017/0101674 A1* | 4/2017 | So et al. .......... C12Q 2531/113 |

FOREIGN PATENT DOCUMENTS

WO     2017/112666 A1    6/2017

OTHER PUBLICATIONS

Bettegowda, et al., "Detection of circulating tumor DNA in early- and late-stage human malignancies", SciTrans Med, vol. 6., No. 224, 2014, pp. 1-11.

Braslavsky, et al., "Sequence information can be obtained from single DNA molecules", PNAS, vol. 100, No. 7, 2003, pp. 3960-3964.

Duncavage, et al., "Hybrid Capture and Next-Generation Sequencing Identify Viral Integration Sites from Formalin-Fixed, Paraffin-Embedded Tissue", J Mol Diagn., vol. 13, No. 3, 2011, pp. 325-333.

Harris, et al., "Single-Molecule DNA Sequencing of a Viral Genome", Science, vol. 320, 2008, pp. 106-109.

Marguiles, et al., "Genome sequencing in microfabricated high-density picolitre reactors", Nature vol. 437, No. 7057, 2005, pp. 376-380.

Maxam, et al., "A new method for sequencing DNA", PNAS, vol. 74, No. 2, 1977, pp. 560-564.

Moudrianakis, et al., "Base Sequence Determinationin Nucleic Acids With The Electron Microscope III. Chemistry and microscopy of guanine-labeled DNA", PNAS, vol. 53, No. 3, 1965, pp. 564-671.

Mouliere, et al., "Circulating tumor-derived DNA is shorter than somatic DNA in plasma", PNAS, vol. 112, No. 11, 2015, pp. 3178-3179.

Mouliere, et al., "Multi-marker Analysis of Circulating Cell-free DNA Toward Personalized Medicine for Colorectal Cancer," Mol Oncol., vol. 8, No. 5, 2014, pp. 927-947.

Newman, et al., "An ultrasensitive method for quantitating circulating tumor DNA with broad patient coverage", Nat Med, vol. 20, No. 5, 2014, pp. 548-554.

Sanger, et al., "DNA sequencing with chain-terminating inhibitors", PNAS, vol. 74, No. 12, 1977, pp. 5463-5467.

(Continued)

*Primary Examiner* — Kaijiang Zhang

(74) *Attorney, Agent, or Firm* — Benjamin C. Pelletier; Haynes and Boone LLP

(57) ABSTRACT

Methods for preparing sequencing libraries from a DNA-containing test sample, as well as methods for correcting sequencing-derived errors, are provided.

20 Claims, 11 Drawing Sheets

(56) References Cited

OTHER PUBLICATIONS

Soni, et al., "Progress toward ultrafast DNA sequencing using solid-state nanopores", Clin. Chem, vol. 53, No. 11, 2007, pp. 1996-2001.

* cited by examiner

METHODS FOR ENRICHING FOR DUPLEX READS IN SEQUENCING AND ERROR CORRECTION

CROSS-REFERENCE TO RELATED APPLICATIONS

Under 35 U.S.C. § 119(e), this application claims priority benefit of the filing date of U.S. Provisional Patent Application No. 62/599,580, filed on Dec. 15, 2017, the disclosure of which application is herein incorporated by reference in its entirety.

FIELD OF THE INVENTION

The present invention relates to molecular biology techniques and methods for preparing sequencing libraries from a DNA-containing test sample, as well as methods for correcting sequencing-derived errors.

BACKGROUND OF THE INVENTION

Analysis of circulating cell-free DNA (cfDNA) using next generation sequencing (NGS) is recognized as a valuable tool for detection and diagnosis of cancer. Identifying rare variants indicative of cancer using NGS often requires deep sequencing of circulating cfDNA from a patient test sample. Alternatively, many tumor-derived variants can also be identified using less expensive, lower depth, whole exome sequencing approaches. However, errors introduced during sample preparation and sequencing can make accurate identification of variants difficult.

Duplexed sequence reads are critical for error correction in sequencing applications that typically use low input levels of material and/or have limited sequencing coverage (e.g., analysis of cfDNA). For error correction, particularly in limited depth exome sequencing, it is important to avoid sequencing non-duplex DNA molecules. Current protocols for preparing a sequencing library from double-stranded DNA typically includes DNA end repair, 3' end A-tailing, ligation of sequencing adapters to the double-stranded (duplexed) DNA, and polymerase chain reaction (PCR) amplification to enrich for adapter ligated DNA molecules. The procedure requires four successful ligation events to obtain sequenceable fragments for both the forward and reverse strands of a double-stranded DNA molecule. If a single ligation event fails during library preparation, one strand of the duplexed library fragment will not be amplified and a non-duplexed read will be observed during sequence analysis. However, as one of skill in the art would readily recognize, these individual ligations events are not 100% efficient, and duplex sequence information from the test sample can be lost. Accordingly, there is a need in the art for new methods of preparing a sequencing library that enrich for duplexed DNA molecules, thereby increasing duplex reads in sequencing.

SUMMARY OF THE INVENTION

In one embodiment, the present invention is directed to a method for preparing a sequencing library from a test sample comprising a plurality of double-stranded DNA molecules or fragments, the method comprising: (a) obtaining a test sample comprising a plurality of double-stranded DNA (dsDNA) molecules, wherein the dsDNA molecules comprise a forward strand and a reverse strand; (b) ligating double-stranded DNA adapters to both ends of the dsDNA molecules generating a plurality of dsDNA adapter-molecule constructs; (c) incorporating one or more biotin-labeled nucleotides into unligated or nicked dsDNA adapter-molecule constructs to create a plurality of labeled dsDNA adapter-molecule constructs; (d) depleting the labeled dsDNA adapter-molecule constructs from the test sample; and (e) amplifying the remaining dsDNA adapter-molecule constructs in the depleted test sample to generate a sequencing library. In accordance with some embodiments of the present invention, the labeled dsDNA adapter-molecule constructs comprising a biotin-labeled strand and the corresponding complementary strand of the duplex DNA are removed (or depleted) from the sample.

In another embodiment, the present invention is directed to a method for correcting sequencing-derived errors in sequence reads, the method comprising: (a) obtaining a test sample comprising a plurality of double-stranded (dsDNA) molecules, wherein the dsDNA molecules comprise a forward strand sequence and a reverse complement strand sequence; (b) preparing a sequencing library, wherein preparing the sequencing library comprises: (i) providing double-stranded DNA (dsDNA) adapters, wherein the dsDNA adapters comprise a unique molecular identifier (UMI); (ii) ligating the adapters to both ends of the plurality of dsDNA molecules to generate a plurality of dsDNA adapter-molecule constructs; (iii) incorporating one or more biotin-labeled nucleotides into unligated or nicked dsDNA adapter-molecule constructs to create a plurality of labeled dsDNA adapter-molecule constructs; (iv) depleting the labeled dsDNA adapter-molecule constructs from the test sample; and (v) amplifying the remaining dsDNA adapter-molecule constructs in the depleted test sample to generate a sequencing library; (c) sequencing at least a portion of the sequencing library to obtain a plurality of sequence reads; (d) grouping the sequence reads into families based on the UMIs, wherein each family comprises a first set of forward strand sequences each having a first UMI and a second set of reverse complement strand sequences each having a second UMI; and (e) comparing the sequence reads within each family to generate a consensus sequence for each family. In accordance with some embodiments of the invention, the labeled dsDNA adapter-molecule constructs comprising a biotin-labeled strand and the corresponding complementary strand of the duplex DNA are removed (or depleted) from the sample.

Aspects of the invention are directed to a method for identifying one or more rare variants from a test sample, the method comprising: (a) obtaining a test sample comprising a plurality of double-stranded (dsDNA) molecules, wherein the dsDNA molecules comprise a forward strand sequence and a reverse complement strand sequence; (b) preparing a sequencing library, wherein preparing the sequencing library comprises: (i) providing double-stranded DNA (dsDNA) adapters, wherein the dsDNA adapters comprise a unique molecular identifier (UMI); (ii) ligating the adapters to both ends of the plurality of dsDNA molecules to generate a plurality of dsDNA adapter-molecule constructs; (iii) incorporating one or more biotin-labeled nucleotides into unligated or nicked dsDNA adapter-molecule constructs to create a plurality of labeled dsDNA adapter-molecule constructs; (iv) depleting the labeled dsDNA adapter-molecule constructs from the test sample; and (v) amplifying the remaining dsDNA adapter-molecule constructs in the depleted test sample to generate a sequencing library; (c) sequencing at least a portion of the sequencing library to obtain a plurality of sequence reads; (d) grouping the sequence reads into families based on the UMIs, wherein each family comprises a first set of forward strand sequences each having a first UMI and a second set of reverse complement strand sequences each having a second UMI; (e) comparing the sequence reads within each family to generate a consensus sequence for each family; and (f) aligning the consensus sequences to a reference sequence and identifying one or more of the consensus sequences as one or more rare variants if the one or more consensus sequences vary from the reference sequence at one or more nucleotide positions. In accordance with some embodiments of the present invention, the labeled dsDNA adapter-molecule constructs comprising a biotin-labeled strand and the corresponding complementary strand of the duplex DNA are removed (or depleted) from the sample.

In some embodiments, the dsDNA molecules are cell-free DNA (cfDNA) molecules. In some embodiments, the cfDNA molecules originate from healthy cells and from cancer cells. In some embodiments, the test sample comprises whole blood, a blood fraction, plasma, serum, urine, fecal matter, saliva, a tissue biopsy, pleural fluid, pericardial fluid, cerebral spinal fluid, peritoneal fluid, or any combination thereof. In some embodiments, the plurality of dsDNA molecules are modified prior to adapter ligation, and wherein the modification comprises end-repairing and A-tailing prior to adapter ligation. In some embodiments, the adapters further comprise a sample-specific index sequence. In some embodiments, the adapters further comprise a universal priming site. In some embodiments, the adapters further comprise one or more sequencing oligonucleotides for use in cluster generation and/or sequencing.

In some embodiments, one or more biotin-labeled nucleotides are incorporated into unligated or nicked dsDNA adapter-molecule constructs using a DNA polymerase. In some embodiments, the DNA polymerase is a DNA polymerase comprising strand displacement activity. In some embodiments, the DNA polymerase lacks exonuclease activity. In some embodiments, the DNA polymerase is *Bacillus stearothermophilus* DNA polymerase (Bst Pol), a Klenow DNA polymerase, or a phi29 DNA polymerase. In some embodiments, the DNA polymerase is a Klenow DNA polymerase that lacks exonuclease activity.

In some embodiments, a consensus sequence comprises a sequence of nucleotide bases, wherein each base is identified at a given position in the sequence when a specific base is present in a majority of the sequence reads of the family. In some embodiments, the consensus sequence comprises a sequence of nucleotide bases, wherein each base is identified at a given position in the sequence when a specific base is present in at least 70%, 80%, 90% or 95% of the sequence reads comprising the family.

In some embodiments, a method comprises loading at least a portion of the sequence library into a sequencing flow cell and generating a plurality of sequencing clusters on the flow cell, wherein the clusters comprise the forward strand sequence and the reverse complement strand sequence. In some embodiments, the sequence reads are obtained from next-generation sequencing (NGS). In some embodiments, the sequence reads are obtained from massively parallel sequencing using sequencing-by-synthesis. In some embodiments, the sequence reads are obtained from paired-end sequencing. In some embodiments, the sequence reads comprise a read pair, wherein each read pair comprises a first read of the forward strand sequence and second read of the reverse complement strand sequence.

In some embodiments, a method further comprises using the one or more variants to detect the presence or absence of a cancer, determine a cancer status, monitor cancer progression, and/or determine a cancer classification. In some embodiments, monitoring cancer progression further comprises monitoring disease progression, monitoring therapy, or monitoring cancer growth. In some embodiments, the cancer classification further comprises determining a cancer type and/or a cancer tissue of origin. In some embodiments, the cancer comprises a carcinoma, a sarcoma, a myeloma, a leukemia, a lymphoma, a blastoma, a germ cell tumor, or any combination thereof.

DEFINITIONS

Figure 1:
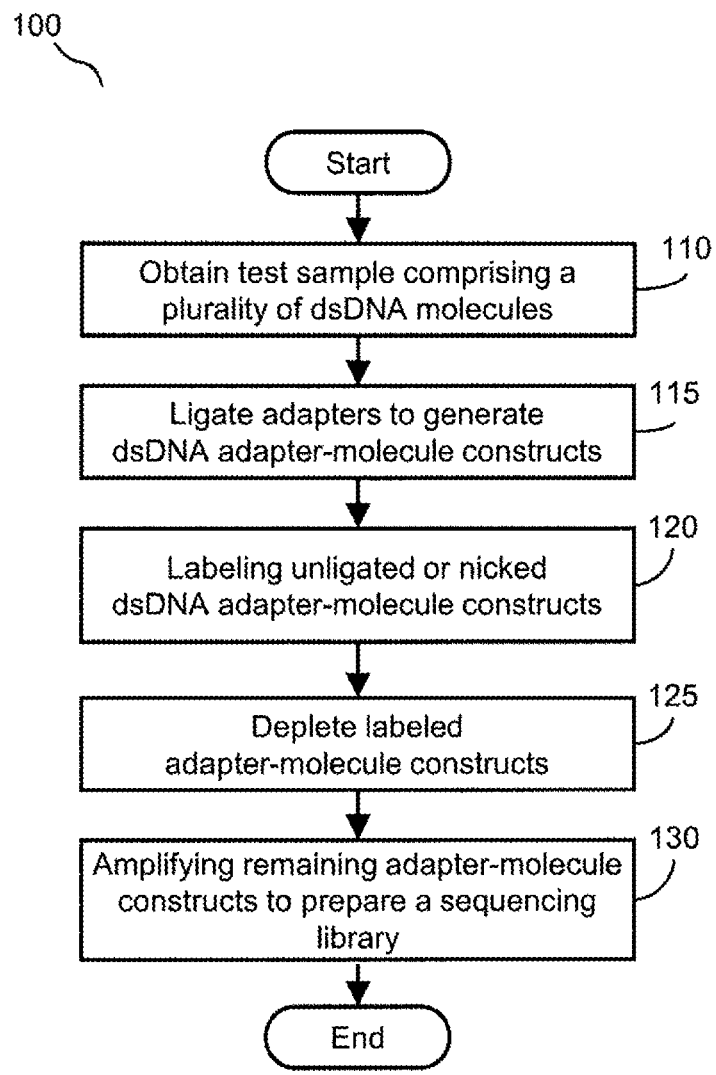
FIG. 1 is a flow diagram illustrating a method of preparing a sequencing library enriched for double-stranded or duplexed DNA molecules, in accordance with one embodiment of the present invention.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application, as do the following, each of which is incorporated by reference herein in its entirety: Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, $6^{th}$ edition (Saunders, 2007).

All publications mentioned herein are expressly incorporated herein by reference to disclose and describe the methods and/or materials in connection with which the publications are cited.

The term "amplicon" as used herein means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase, or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references, each of which are incorporated herein by reference herein in their entirety: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g., "real-time PCR", or "real-time NASBA" as described in Leone et al, Nucleic Acids Research, 26: 2150-2155 (1998), and like references.

As used herein, the term "amplifying" means performing an amplification reaction. A "reaction mixture" means a solution containing all the necessary reactants for performing a reaction, which may include, but is not be limited to, buffering agents to maintain pH at a selected level during a reaction, salts, co-factors, scavengers, and the like.

The terms "fragment" or "segment", as used interchangeably herein, refer to a portion of a larger polynucleotide molecule. A polynucleotide, for example, can be broken up, or fragmented into, a plurality of segments, either through natural processes, as is the case with, e.g., cfDNA fragments that can naturally occur within a biological sample, or through in vitro manipulation. Various methods of fragmenting nucleic acids are well known in the art. These methods may be, for example, either chemical or physical or enzymatic in nature. Enzymatic fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave a polynucleotide at known or unknown locations. Physical fragmentation methods may involve subjecting a polynucleotide to a high shear rate. High shear rates may be produced, for example, by moving DNA through a chamber or channel with pits or spikes, or forcing a DNA sample through a restricted size flow passage, e.g., an aperture having a cross sectional dimension in the micron or submicron range. Other physical methods include sonication and nebulization. Combinations of physical and chemical fragmentation methods may likewise be employed, such as fragmentation by heat and ion-mediated hydrolysis. See, e.g., Sambrook et al., "Molecular Cloning: A Laboratory Manual," 3rd Ed. Cold Spring Harbor Laboratory Press, Cold Spring Harbor, N.Y. (2001) ("Sambrook et al.") which is incorporated herein by reference for all purposes. These methods can be optimized to digest a nucleic acid into fragments of a selected size range.

The terms "polymerase chain reaction" or "PCR", as used interchangeably herein, mean a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors that are well-known to those of ordinary skill in the art, e.g., exemplified by the following references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including, but not limited to, RT-PCR, real-time PCR, nested PCR, quantitative PCR, multiplexed PCR, and the like. The particular format of PCR being employed is discernible by one skilled in the art from the context of an application. Reaction volumes can range from a few hundred nanoliters, e.g., 200 nL, to a few hundred μL, e.g., 200 μL. "Reverse transcription PCR," or "RT-PCR," means a PCR that is preceded by a reverse transcription reaction that converts a target RNA to a complementary single stranded DNA, which is then amplified, an example of which is described in Tecott et al, U.S. Pat. No. 5,168,038, the disclosure of which is incorporated herein by reference in its entirety. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); the disclosures of which are hereby incorporated by reference herein in their entireties. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Asymmetric PCR" means a PCR wherein one of the two primers employed is in great excess concentration so that the reaction is primarily a linear amplification in which one of the two strands of a target nucleic acid is preferentially copied. The excess concentration of asymmetric PCR primers may be expressed as a concentration ratio. Typical ratios are in the range of from 10 to 100. "Multiplexed PCR" means a PCR wherein multiple target sequences (or a single target sequence and one or more reference sequences) are simultaneously carried out in the same reaction mixture, e.g., Bernard et al, Anal. Biochem., 273: 221-228 (1999)(two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, β-microglobulin, ribosomal RNA, and the like. Techniques for quantitative PCR are well-known to those of ordinary skill in the art, as exemplified in the following references, which are incorporated by reference herein in their entireties: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); and Becker-Andre et al, Nucleic Acids Research, 17: 9437-9446 (1989).

The term "primer" as used herein means an oligonucleotide, either natural or synthetic, that is capable, upon forming a duplex with a polynucleotide template, of acting as a point of initiation of nucleic acid synthesis and being extended from its 3'-end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually, primers are extended by a DNA polymerase. Primers usually have a length in the range of from 14 to 40 nucleotides, or in the range of from 18 to 36 nucleotides. Primers are employed in a variety of nucleic acid amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following reference that is incorporated by reference herein in its entirety: Dieffenbach, editor, PCR Primer: A Laboratory Manual, $2^{nd}$ Edition (Cold Spring Harbor Press, New York, 2003).

The terms "unique sequence tag", "sequence tag", "tag", "unique molecular identifier", "UMI", or "barcode", as used interchangeably herein, refer to an oligonucleotide that is attached to a polynucleotide or template molecule and is used to identify and/or track the polynucleotide or template in a reaction or a series of reactions. A sequence tag may be attached to the 3'- or 5'-end of a polynucleotide or template, or it may be inserted into the interior of such polynucleotide or template to form a linear conjugate, sometimes referred to herein as a "tagged polynucleotide," or "tagged template," or the like. Sequence tags may vary widely in size and compositions; the following references, which are incorporated herein by reference in their entireties, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g., via a hybridization reaction or via an enzymatic reaction, such as sequencing; whether they are labeled, e.g., with a fluorescent dye or the like; the number of distinguishable oligonucleotide tags required to unambiguously identify a set of polynucleotides, and the like, and how different the tags of a particular set must be in order to ensure reliable identification, e.g., freedom from cross hybridization or misidentification from sequencing errors. In one aspect, sequence tags can each have a length within a range of from about 2 to about 36 nucleotides, or from about 4 to about 30 nucleotides, or from about 4 to about 20 nucleotides, or from about 8 to about 20 nucleotides, or from about 6 to about 10 nucleotides. In one aspect, sets of sequence tags are used, wherein each sequence tag of a set has a unique nucleotide sequence that differs from that of every other tag of the same set by at least two bases; in another aspect, sets of sequence tags are used wherein the sequence of each tag of a set differs from that of every other tag of the same set by at least three bases.

The term "enrich" as used herein means to increase a proportion of one or more target nucleic acids in a sample. An "enriched" sample or sequencing library is therefore a sample or sequencing library in which a proportion of one of more target nucleic acids has been increased with respect to non-target nucleic acids in the sample.

The term "deplete" as used herein means to decrease a proportion of one or more target nucleic acids in a sample. A "depleted" sample or sequencing library is therefore a sample or sequencing library in which a proportion of one of more target nucleic acids has been decreased with respect to non-target nucleic acids in the sample.

The terms "subject" and "patient" are used interchangeably herein and refer to a human or non-human animal who is known to have, or potentially has, a medical condition or disorder, such as, e.g., a cancer.

The term "sequence read" as used herein refers to nucleotide sequences read from a sample obtained from a subject. Sequence reads can be obtained through various methods known in the art.

The terms "circulating tumor DNA" or "ctDNA" and "circulating tumor RNA" or "ctRNA" refer to nucleic acid fragments (DNA or RNA) that originate from tumor cells or other types of cancer cells, which may be released into a subject's bloodstream as a result of biological processes, such as apoptosis or necrosis of dying cells, or may be actively released by viable tumor cells.

DETAILED DESCRIPTION OF THE INVENTION

Aspects of the invention relate to a method for enriching duplexed DNA molecules during sequencing library preparation, thereby increasing duplex reads in subsequent sequencing analysis. Methods in accordance with embodiments of the invention use a labeling and pull-down strategy to specifically remove (or deplete) unwanted nucleic acid molecules during library preparation. For example, nucleic acid molecules containing a failed ligation event and/or nucleic acid molecules having unrepaired damage (e.g., gap or nick site) can be removed using the labeling and pulldown strategy of the present invention prior to subsequent amplification of the nucleic acid molecules.

In some embodiments, adapter-molecule constructs containing a failed ligation event or unrepaired damage (e.g., a gap or nick) are labeled with one or more labeled dNTP (e.g., biotin-dUTP) using a nick translation reaction and/or a primer extension reaction. The labeled strand and its strand partner are then removed (or depleted) from the library (e.g., using a streptavidin bead pull-down protocol). Removal of these unwanted, unligated or nicked dsDNA adapter-molecule constructs enriches the sequencing library for dsDNA or duplex molecules, thereby enriching for sequencable, double-stranded or duplexed DNA molecules in subsequent sequencing steps. Double-stranded DNA (or duplex) molecules having no failed ligations and/or no unrepaired damage (gap or nick site) remain and can be amplified (e.g., using PCR amplification), thereby enriching fully ligated, and sequencable, double-stranded DNA (or duplexed) molecules. Accordingly, as the sequencing library is enriched for duplexed DNA molecules, recovery of duplexed sequencing reads (i.e., sequencing reads of both the forward (+) and reverse (−) complement strands) in the sequencing library is improved, thereby increasing duplex sequence reads in subsequent sequencing analysis.

FIG. 1 is a flow diagram illustrating a method 100 of preparing a sequencing library enriched for double-stranded or duplexed DNA molecules, in accordance with one embodiment of the present invention. As previously described, four successful ligation events are required to obtain sequencable fragments for both the forward and reverse strands of a duplex DNA molecule. However, as one of skill in the art would readily recognize, these individual ligation events are not 100% efficient, and sequence information from the test sample can be lost. Method 100 employs a labeling and pulldown approach to remove or deplete undesired DNA molecules (e.g., unligated DNA molecules) during library preparation. As described elsewhere herein, the method can be used to remove or deplete DNA molecules containing a failed ligation event and/or nucleic acid molecules having unrepaired damage (e.g., gap or nick site).

At step 110, a DNA test sample comprising a plurality of double-stranded DNA (dsDNA) molecules comprising a forward (+) strand sequence and a reverse (−) complement strand sequence are obtained from a subject (e.g., a patient). In one embodiment, the test sample may be a biological test sample selected from the group consisting of blood, plasma, serum, urine, saliva, fecal matter, and any combination thereof. In another embodiment, the test sample may be a biological test sample including one or more cells (e.g., blood cells). Alternatively, in still another embodiment, the test sample or biological test sample may comprise a test sample selected from the group consisting of whole blood, a blood fraction, a tissue biopsy, pleural fluid, pericardial fluid, cerebral spinal fluid, peritoneal fluid, and any combination thereof. In other embodiments, the sample is a plasma sample from a cancer patient, or a patient suspected of having cancer. In accordance with some embodiments, the test sample or biological test sample comprises a plurality of cell-free nucleic acids (e.g., cell-free DNA (cfDNA) and/or cell-free RNA (cfRNA)) fragments. In other embodiments, the test sample or biological test sample comprises a plurality of cell-free nucleic acid (e.g., cell-free DNA and RNA) fragments originating from healthy cells and from cancer cells. Optionally, in one embodiment, cell-free nucleic acids (e.g., cfDNA and/or cfRNA) can be extracted and/or purified from the test sample before proceeding with subsequent library preparation steps. In general, any known method in the art can be used to extract and purify cell-free nucleic acids from the test sample. For example, cell-free nucleic acids can be extracted and purified using one or more known commercially available protocols or kits, such as the QIAamp circulating nucleic acid kit (Qiagen). In some embodiments, the sample can be, for example, a fragmented genomic DNA (gDNA) sample (e.g., a sheared gDNA sample).

At step 120, double-stranded DNA (dsDNA) adapters are ligated to both ends of the double-stranded DNA (dsDNA) molecules to generate dsDNA adapter-molecule constructs. The ligation reaction can be performed using any suitable ligation step (e.g., using a ligase) which joins the dsDNA adapters to the dsDNA molecules to form dsDNA adapter-molecule constructs. In one example, the ligation reaction is performed using T4 DNA ligase. In another example, T7 DNA ligase is used for adapter ligation to the dsDNA molecules. In still another example, T3 DNA ligase can be used for adapter ligation. Optionally, the double-stranded DNA (dsDNA) molecules are modified for adapter ligation. For example, the ends of dsDNA molecules are repaired using, for example, T4 DNA polymerase and/or Klenow polymerase and phosphorylated with a polynucleotide kinase enzyme prior to ligation of the adapters. A single "A" deoxynucleotide is then added to the 3′ ends of dsDNA molecules using, for example, Taq polymerase enzyme, producing a single base 3′ overhang that is complementary to a 3′ base (e.g., a T) overhang on the dsDNA adapter. In still another embodiment, the complementary 3′ overhang can be added to the dsDNA molecule using Klenow exo-.

In one embodiment, the adapters can include a unique molecular identifier (UMI) sequence, such that, after library preparation, the sequencing library will include UMI tagged amplicons derived from unique dsDNA molecules or dsDNA fragments. In one embodiment, unique sequence tags (e.g., unique molecular identifiers (UMIs)) can be used to identify unique nucleic acid sequences from a test sample.

For example, differing unique sequence tags (UMIs) can be used to differentiate various unique dsDNA molecules originating from the test sample. In another embodiment, the UMI sequences can be used to identify both strands or duplex sequence reads from a dsDNA molecule (i.e., the single-strand forward (+) and single-strand reverse (−) complement strand sequences originating for a single dsDNA molecule). In still another embodiment, unique sequence tags (UMIs) can be used to reduce amplification bias, which is the asymmetric amplification of different targets due to differences in nucleic acid composition (e.g., high GC content). The unique sequence tags (UMIs) can also be used to discriminate between nucleic acid mutations that arise during amplification. In one embodiment, the unique sequence tag can comprise a short oligonucleotide sequence having a length of from about 2 nt to about 100 nt, from about 2 nt to about 60 nt, from about 2 to about 40 nt, or from about 2 to about 20 nt. In another embodiment, the UMI tag can comprise a short oligonucleotide sequence greater than about 5, 6, 7, 8, 9, 10, 11, 12, 13, 14, 15, 16, 17, or 18 nucleotides (nt) in length.

The unique sequence tags can be present in a multifunctional nucleic acid sequencing adapter comprising a unique sequence identifier (UMI), a sample-specific index sequence (or barcode), and/or one or more primer binding sites (e.g., one or more universal priming sites). In one embodiment, the sequencing adapters utilized may include a universal primer and/or one or more sequencing oligonucleotides for use in subsequent cluster generation and/or sequencing (e.g., known P5 and P7 sequences for use in sequencing by synthesis (SBS) (Illumina, San Diego, Calif.)). In another embodiment, the adapter includes a sample-specific index sequence (or barcode), such that, after library preparation, the library can be combined with one or more other libraries prepared from individual samples, thereby allowing for multiplex sequencing. The sample-specific index sequence can comprise a short oligonucleotide sequence having a length of from about 2 nt to about 20 nt, from about 2 nt to about 10 nt, from about 2 to about 8 nt, or from about 2 to about 6 nt. In another embodiment, the sample-specific index sequence can comprise a short oligonucleotide sequence greater than about 2, 3, 4, 5, 6, 7, or 8 nucleotides (nt) in length. In another embodiment, the sample-specific index sequence (or barcode) can be added to the dsDNA adapter-molecule constructs during a subsequent library preparation step (e.g., via a primer during PCR amplification).

As shown in FIG. 1, at step 125, unligated or nicked dsDNA adapter-molecule constructs are labeled for subsequent removal or depletion from the sample. For example, in one embodiment, dsDNA adapter-molecule constructs containing a failed adapter ligation event and/or an unrepaired gap/nick site can be labeled with one or more labeled dNTP (e.g., biotin-dUTP) using a nick translation reaction. The nick translation reaction utilizes the free 3'-end of the unligated adapter, or the 3'-end of the dsDNA molecule, in an extension reaction to incorporate the one or more labeled dNTPs. In another embodiment, a primer extension reaction can be used to label the dsDNA adapter-molecule constructs containing a failed adapter ligation event and/or an unrepaired gap/nick site can be labeled with a labeled dNTP (e.g., biotin-dUTP). For example, a primer can be annealed to the ligated strand of a dsDNA adapter-molecule construct, and extended in a polymerization reaction incorporating the one or more labeled dNTPs (e.g., biotin-dUTP). In the practice of this embodiment, a primer having a free 3'-OH is used in the primer extension reaction. The primer sequence can comprise a short oligonucleotide sequence having a length of from about 2 nt to about 50 nt, from about 2 nt to about 40 nt, from about 2 to about 30 nt, from about 2 to about 20 nt, or from about 2 to about 10 nt. In another embodiment, the primer sequence can comprise a short oligonucleotide sequence greater than about 2, 3, 4, 5, 6, 7, 8, 9, or 10 nucleotides (nt) in length. In still another embodiment, the primer can include one or more biotin-labeled dNTPs. For example, a biotin-labeled dNTP can be added to the 5'-end of the primer and used for subsequent removal or depletion of the labeled adapter-molecule construct.

In both the nick translation and primer extension reaction, a strand complementary to the ligated strand of the dsDNA adapter-molecule construct is synthesized by a DNA polymerase, utilizing the ligated strand as a template, in the presence of a reaction mixture comprising one or more labeled dNTPs. In general, any DNA polymerase can be used in the step. In one embodiment, the DNA polymerase is a DNA polymerase with strand displacement activity. For example, the DNA polymerase may be *Bacillus stearothermophilus* DNA polymerase (Bst Pol) (available from Clontech) or may be phi29 DNA polymerase (available from New England BioLabs, Inc.). In some embodiments, a DNA polymerase having 5'→3' polymerase activity, but lacking exonuclease activity (e.g., 5'→3' and/or 3'→5' exonuclease activity) (exo-), and a dNTP mix that includes one or more labeled dNTPs is used to label molecules or fragments containing a failed ligation event or an unrepaired gap/nick site. For example, a reaction mix including biotin-labeled dUTP (biotin-dUTP) can be used to label the unligated or nicked DNA molecule with biotin-dUTP. In other embodiments, the biotin-labeled dNTP can be biotin-dATP, biotin-dCTP, biotin-dGTP, and/or biotin-dUTP. In one embodiment, the DNA polymerase is Klenow Fragment (3'→5' exo-). In another embodiment, the DNA polymerase is Bst 3.0 DNA polymerase. In some embodiments, the selection of a particular DNA polymerase enzyme results in an increased percentage of duplex DNA recovered from the reaction, as described further in Example 2. Specifically, in certain embodiments, the selection of a particular DNA polymerase enzyme increases the percentage of duplex DNA recovered from the reaction by an amount that ranges from about 10% to about 25%, such as about 11%, 12%, 13%, 14%, 15%, 16%, 17%, 18%, 19%, 20%, 21%, 22%, 23%, or about 24%. In some embodiments, the methods involve the use of a Klenow DNA polyermase enzyme that lacks exonuclease activity (Klenow exo-), which increases the percentage of duplex DNA yield from about 30% to about 80%, from about 40% to about 75%, from about 50% to about 60%, or from about 50% to about 65% or to about 70%.

At a step 125, a pull-down protocol is performed to remove (or deplete) labeled dsDNA adapter-molecule constructs. For example, as described above, a reaction mixture including one or more biotin-labeled dNTP can be used to label unligated or nicked dsDNA adapter-molecules constructs obtained from step 115. The biotin-labeled dsDNA adapter-molecule constructs can then be removed (or depleted) from the sample using a streptavidin pull-down protocol. For example, the biotin label may be used for immobilization or isolation of the adapter-molecule constructs using a streptavidin-coated surface (e.g., streptavidin-coated beads). Immobilization of biotinylated molecules onto streptavidin capture beads can be used to capture and deplete the adapter-molecule constructs from the test sample. The streptavidin pull-down protocol immobilizes or removes the biotin-dNTP labeled adapter-molecule constructs, allowing the fully ligated adapter-constructs to remain in the test sample. In accordance with some embodiments of the present invention, the labeled dsDNA adapter-molecule constructs comprising a biotin-labeled strand and the corresponding complementary strand of the duplex DNA are removed (or depleted) from the sample.

At step 130, the remaining dsDNA adapter-molecule constructs (i.e., unlabeled adapter-molecule constructs) in the sample are amplified to generate a sequencing library. For example, the adapter-molecule constructs can be amplified by PCR using a DNA polymerase and a reaction mixture containing one or more primers and a mixture of dNTPs (i.e., dATP, dCTP, dGTP, and dTTP). As unligated or nicked adapter-molecule constructs are removed (depleted) in step 125, only fully ligated adapter-molecule constructs remain in the test sample.

Figure 2:
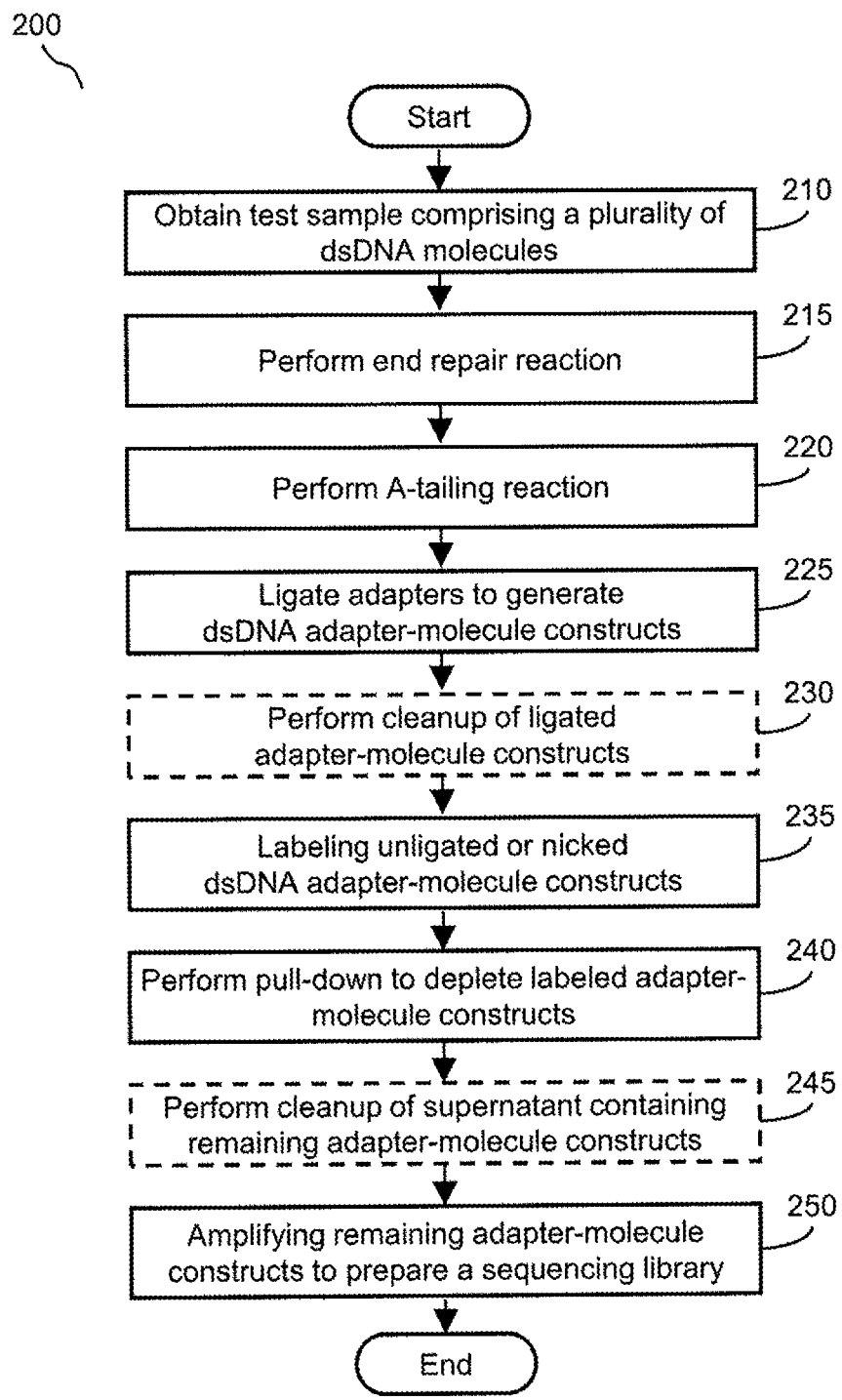
FIG. 2 is a flow diagram illustrating a method of preparing a sequencing library enriched for double-stranded or duplexed DNA molecules, in accordance with another embodiment of the present invention.

FIG. 2 is a flow diagram illustrating a method 200 of removing or depleting unligated or nicked dsDNA fragments (e.g., fragments containing a failed ligation event or unrepaired gap/nick site) for improved duplex sequencing. As previously noted, four successful ligation events are required to obtain sequencable fragments for both the forward and reverse strands of a duplex DNA fragment. As the sequencing library is enriched for duplexed DNA molecules, recovery of duplexed sequencing reads (i.e., sequencing reads of both the forward (+) and reverse (−) complement strands) in the sequencing library is improved, thereby increasing duplex sequence reads in subsequent sequencing analysis. Method 200 includes, but is not limited to, the following steps.

At a step 210, a test sample comprising double-stranded DNA (dsDNA) molecules is obtained from a subject (e.g., a patient). As noted above, the test sample may be a biological test sample selected from the group consisting of blood, plasma, serum, urine, saliva, fecal matter, and any combination thereof. Alternatively, the test sample or biological test sample may comprise a test sample selected from the group consisting of whole blood, a blood fraction, a tissue biopsy, pleural fluid, pericardial fluid, cerebral spinal fluid, peritoneal fluid, and any combination thereof. In other embodiments, the sample is a plasma sample from a cancer patient, or a patient suspected of having cancer. In accordance with some embodiments, the test sample or biological test sample comprises a plurality of cell-free nucleic acids (e.g., cell-free DNA (cfDNA) and/or cell-free RNA (cfRNA)) fragments. In other embodiments, the test sample or biological test sample comprises a plurality of cell-free nucleic acid (e.g., cell-free DNA and RNA) fragments originating from healthy cells and from cancer cells. Optionally, in one embodiment, cell-free nucleic acids (e.g., cfDNA and/or cfRNA) can be extracted and/or purified from the test sample before proceeding with subsequent library preparation steps. The sample can be, for example, a cell-free DNA (cfDNA) sample or a fragmented genomic DNA (gDNA) sample (e.g., a sheared gDNA sample).

At step 215, the double-stranded DNA (dsDNA) molecules are modified for adapter ligation. For example, as shown in FIG. 2, the ends of dsDNA molecules are repaired using, for example, T4 DNA polymerase and/or Klenow polymerase and phosphorylated with a polynucleotide kinase enzyme prior to ligation of the adapters.

At step 220, a single "A" deoxynucleotide is then added to the 3' ends of dsDNA molecules using, for example, Taq polymerase enzyme, producing a single base 3' overhang that is complementary to a 3' base (e.g., a T) overhang on the dsDNA adapter.

At step 225, adapters are ligated to both ends of the dsDNA molecules generating a plurality of dsDNA adapter-molecule constructs. The ligation reaction can be performed using any suitable ligation step (e.g., using a ligase) which joins the dsDNA adapters to the dsDNA molecules to form circular adapter-dsDNA-adapter constructs. In one example, the ligation reaction is performed using T4 DNA ligase. In another example, T7 DNA ligase is used for adapter ligation to the dsDNA molecules. As described above, the adapters can include a unique molecular identifier (UMI) sequence, such that, after library preparation, the sequencing library will include UMI tagged amplicons derived from unique dsDNA molecules or dsDNA fragments. In other embodiments, the adapter may also include a sample-specific index sequence (or tag), and/or one or more primer binding sites (e.g., a universal priming site), as described above in reference to FIG. 1.

At step 230, optionally, a cleanup protocol (e.g., an SPRI purification protocol) is performed to isolate or purify the adapter-molecule constructs.

At step 235, unligated or nicked dsDNA adapter-molecule constructs are labeled for subsequent removal or depletion from the sample. For example, as described above, a nick translation reaction, or a primer extension reaction, can be used to label the dsDNA adapter-molecule constructs containing a failed adapter ligation event and/or an unrepaired gap/nick site can be labeled with one or more labeled dNTP (e.g., biotin-dUTP). In both the nick translation and primer extension reaction, a strand complementary to the ligated strand of the dsDNA adapter-molecule construct is synthesized by a DNA polymerase, utilizing the ligated strand as a template, in the presence of a reaction mixture comprising one or more labeled dNTPs. In general, any DNA polymerase can be used in the step. In one embodiment, the DNA polymerase is a DNA polymerase with strand displacement activity. For example, the DNA polymerase may be *Bacillus stearothermophilus* DNA polymerase (Bst Pol) (available from Clontech) or may be phi29 DNA polymerase (available from New England BioLabs, Inc.). In some embodiments, a DNA polymerase having 5'→3' polymerase activity, but lacking exonuclease activity (e.g., 5'→3' and/or 3'→5' exonuclease activity) (exo −), and a dNTP mix that includes one or more labeled dNTPs is used to label fragments containing a failed ligation event or an unrepaired gap/nick site. For example, a reaction mix including biotin-labeled dUTP (biotin-dUTP) can be used to label the unligated or nicked DNA molecule with biotin-dUTP. In other embodiments, the biotin-labeled dNTP can be biotin-dATP, biotin-dCTP, biotin-dGTP, and/or biotin-dUTP. In some embodiments, the DNA polymerase is Klenow Fragment (3'→5' exo −). In another example, the DNA polymerase is Bst 3.0 DNA polymerase.

At step 240, a pull-down protocol is performed to remove (or deplete) labeled adapter-molecule constructs. For example, as described above, a reaction mixture including one or more biotin-labeled dNTP can be used to label unligated or nicked dsDNA adapter-molecule constructs obtained from step 225. The biotin-labeled adapter-molecule constructs can then be removed (or depleted) from the sample using a streptavidin pull-down protocol. For example, the biotin label may be used for immobilization or isolation of the adapter-molecule constructs using a streptavidin-coated surface (e.g., streptavidin-coated beads). Immobilization of biotinylated molecules onto streptavidin capture beads can be used to capture and deplete the adapter-molecule constructs from the test sample. The streptavidin pull-down protocol immobilizes or removes the biotin-dNTP labeled adapter-molecule constructs allowing the fully ligated adapter-molecule constructs to remain in the test sample. In accordance with some embodiments of the present invention, the labeled dsDNA adapter-molecule constructs comprising a biotin-labeled strand and the corresponding complementary strand of the duplex DNA are removed (or depleted) from the sample.

At step 245, optionally, a cleanup protocol (e.g., an SPRI purification protocol) is performed on the remaining supernatant of the test sample to isolate or purify the fully ligated adapter-molecule constructs.

At step 250, the remaining dsDNA adapter-molecule constructs (i.e., unlabeled adapter-molecule constructs) in the sample are amplified to generate a sequencing library. For example, the adapter-molecule constructs can be amplified by PCR using a DNA polymerase and a reaction mixture containing one or more primers and a mixture of dNTPs (i.e., dATP, dCTP, dGTP, and dTTP). As unligated or nicked adapter-molecule constructs are removed (depleted) in step 240, only fully ligated adapter-molecule constructs remain in the test sample.

Figure 3A:
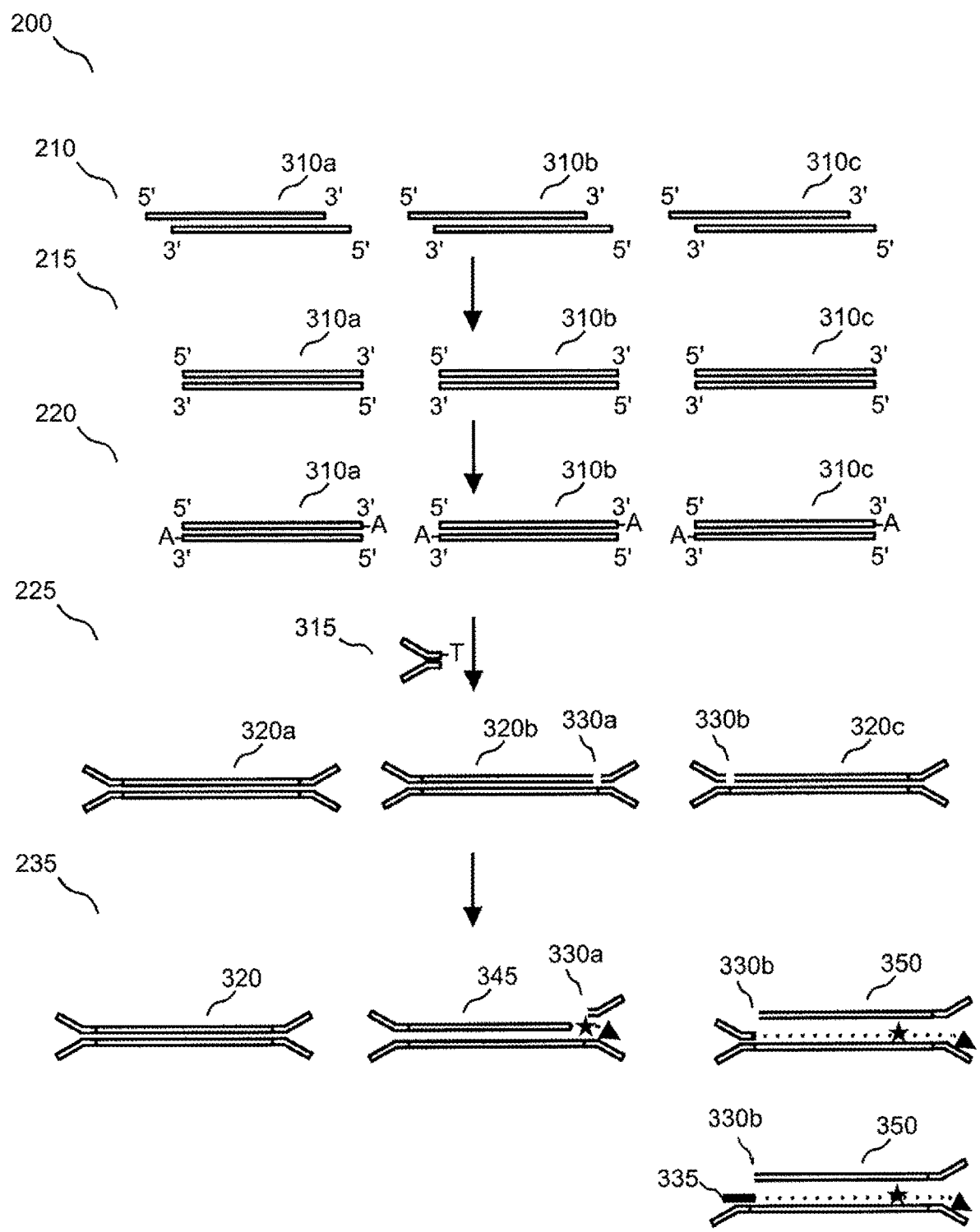
FIGS. 3A and 3B are schematics showing pictorially some of the steps of the method of FIG. 2.
Figure 3B:
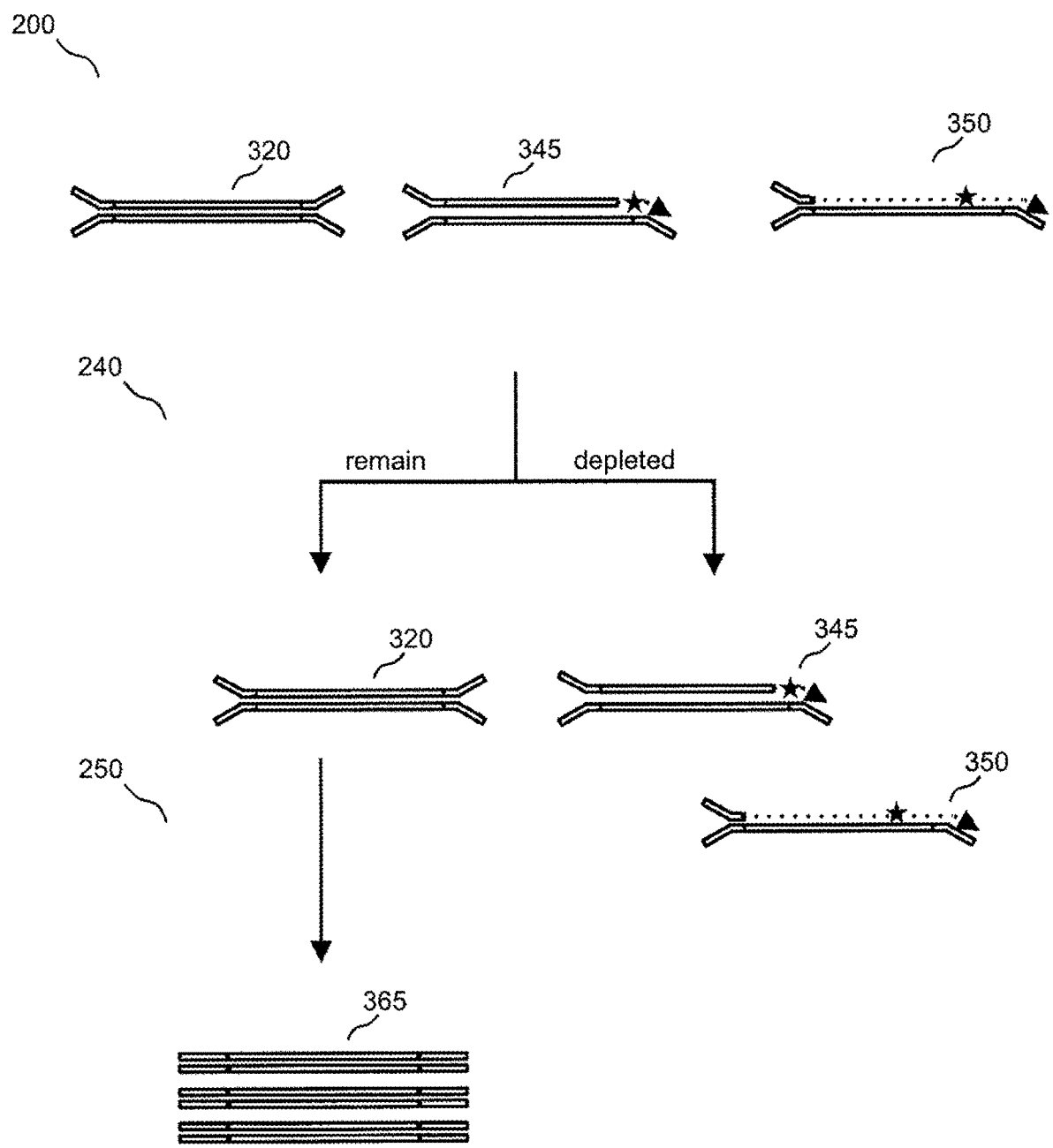

FIGS. 3A and 3B are schematics showing pictorially some of the steps of method 200 of FIG. 2. Namely, at step 210, a sample that includes duplexed DNA molecules 310 is obtained. As shown in FIG. 3A, the test sample may comprise a mixture of three different duplexed DNA molecules 310 each having a 5'-end overhangs (i.e., DNA molecules 310a, 310b, and 310c).

At step 215, an enzymatic repair reaction is performed to repair damage and convert the 5' overhangs on DNA molecules 310 to blunt-ends for subsequent A-tailing and adapter ligation.

At step 220, an A-tailing reaction is performed to add a single "A" nucleotide to the 3' ends of the blunt-ended DNA molecules 310 producing a single "A" base 3' overhang.

At step 225, an adapter 315 comprising a single 3' T base overhang is ligated to the ends of the A-tailed DNA molecules 310. The ligation reaction can be performed using any suitable ligation step (e.g., using a T4 DNA ligase) which joins a copy of the adapter 315 to both ends of the dsDNA molecules 310 to form a plurality of adapter-molecule constructs 320. Three adapter-molecule constructs are shown in FIG. 3A: a (1) a fully ligated adapter-molecule construct 320a having adapters ligated successfully to both ends of the dsDNA molecule (i.e., all four fragment ends are successfully ligated to adapters); (2) an adapter-molecule construct 320b that includes a single failed ligation event 330a at a 3' end of the original dsDNA molecule; and (3) an adapter-molecule construct 320c that includes a single failed ligation event 330b between at the 3' end of the adapter and the a 5' end of the original dsDNA molecule.

At step 235, adapter-molecule constructs containing a failed ligation event (or an unrepaired gap/nick site) are labeled with biotin-dUTP. For example, as shown, a DNA polymerase and a dNTP mix that includes biotin-dUTP (i.e., dATP, dCTP, dGTP, and biotin-dUTP) can be used in a nick translation reaction to label the adapter-molecule constructs. Alternatively, as described above, the adapter-molecule constructs can be labeled using a primer extension reaction. For example, in one embodiment, an extension primer 335 can be used to label fragments containing a failed ligation site (or unrepaired gap/nicked site) with biotin-dUTP. As shown in FIG. 3A, the primer 335 is annealed to the fully ligated strand of the adapter-molecule construct 350 and extended by a DNA polymerase in a primer extension reaction from the 3' end of the primer in the presence of a dNTP mix that includes biotin-dUTP (i.e., dATP, dCTP, dGTP, and biotin-dUTP) to label the dsDNA adapter-molecule constructs. Furthermore, as shown in FIG. 3A, the unligated strand of the original dsDNA molecule is displaced by the DNA polymerase as primer extension proceeds. In still another embodiment, the adapter-molecule constructs can be labeled using a combination of the free 3' end of the unligated adapter and a primer (not shown). In one embodiment, the DNA polymerase contains 5'→3' polymerase activity, but lacks 5'→3' and 3'→5' exonuclease activity. As shown in FIGS. 3A and 3B, two biotin-dUTP labeling constructs are shown: (1) a biotin-dUTP (indicated by a star) labeled adapter-molecule construct 345 derived from adapter-molecule construct 320b that includes a failed ligation event 330a at a 3' end of the dsDNA molecule; and (2) a biotin-dUTP labeled adapter-molecule construct 350 derived from an adapter-molecule construct 320c that includes a failed ligation event 330b between the 3' end of the adapter and the 5' end of the dsDNA molecule or fragment.

At step 240, a streptavidin pull-down protocol is performed to capture and deplete biotin-dUTP labeled adapter-molecule constructs 345 and 350 from the library preparation. As described above, the streptavidin pull-down protocol removes biotin-dUTP labeled adapter-molecule constructs 345 and 350 from the test sample, while fully ligated adapter-constructs 320 remain. As described elsewhere herein, in some embodiments, the labeled dsDNA adapter-molecule constructs comprising a biotin-labeled strand and the corresponding complementary strand of the duplex DNA are removed (or depleted) from the sample.

At step 250, a PCR amplification reaction is performed to amplify and enrich the fully ligated adapter-molecule constructs 320 generating a sequencing library 365 comprising duplexed DNA molecules for subsequent sequencing.

Figure 4:
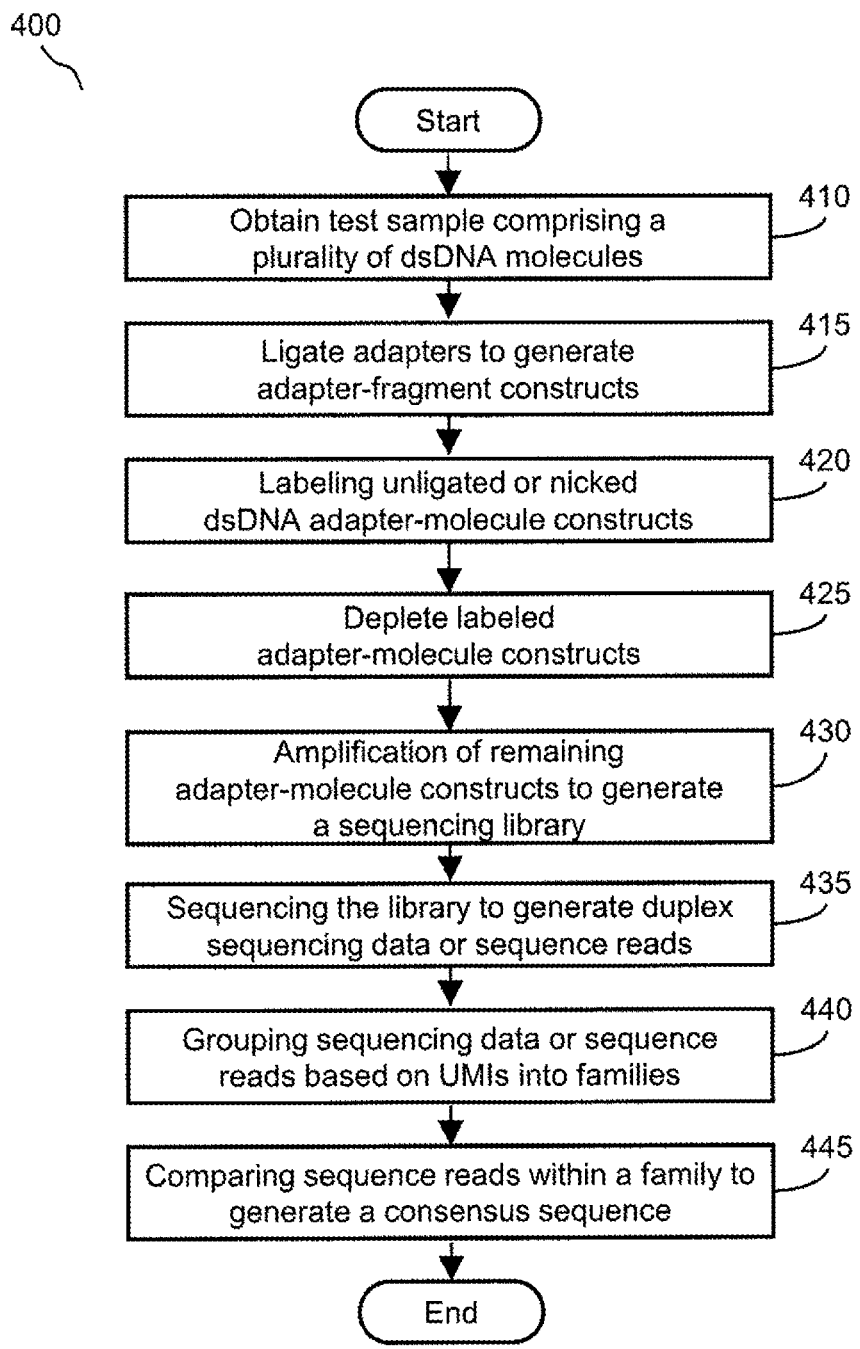
FIG. 4 is a flow diagram illustrating a method for error correction using a sequencing library prepared in accordance with the method of FIG. 1.

FIG. 4 is a flow diagram illustrating a method 400 for preparing an improved sequencing library for duplex sequencing-based error correction.

As shown in FIG. 4, at step 410, a biological test sample comprising a plurality of double-stranded DNA (dsDNA) molecules is obtained from a subject (e.g., a patient known to have or suspected of having cancer). As discussed in more detail elsewhere herein, the biological sample can be a blood, plasma, serum, urine, saliva samples, or any combination thereof. Alternatively, as noted above, the biological sample can be a whole blood, a blood fraction, a tissue biopsy, a pleural fluid, pericardial fluid, a cerebral spinal fluid, a peritoneal fluid, or any combination thereof. In accordance with some embodiments, the biological test sample can comprise a plurality of cell-free nucleic acids (e.g., cell-free DNA (cfDNA)) fragments. In some embodiments, the sample is a plasma sample from a cancer patient, or a patient suspected of having cancer. Optionally, the cell-free nucleic acids (e.g., cfDNA) can be extracted and/or purified from the biological test sample using any means known in the art.

Optionally, the double-stranded DNA (dsDNA) molecules are modified for adapter ligation. For example, the ends of dsDNA molecules are repaired using, for example, T4 DNA polymerase and/or Klenow polymerase and phosphorylated with a polynucleotide kinase enzyme prior to ligation of the adapters. A single "A" deoxynucleotide is then added to the 3' ends of dsDNA molecules using, for example, Taq polymerase enzyme, producing a single base 3' overhang that is complementary to a 3' base (e.g., a T) overhang on the dsDNA adapter.

At step 415 double-stranded DNA (dsDNA) adapters are ligated to both ends of the dsDNA molecules to generate adapter-molecule constructs. The ligation reaction can be performed using any suitable ligation step (e.g., using a ligase) which joins the dsDNA adapters to the dsDNA molecules to form circular adapter-dsDNA-adapter constructs. In one embodiment, the ligation reaction is performed using T4 DNA ligase. In another embodiment, T7 DNA ligase is used for adapter ligation to the dsDNA molecules. As described elsewhere herein, the adapters can comprise a unique molecular identifier (UMI). Furthermore, as noted elsewhere in this disclosure, the adapters can also include one or more primer binding sites (e.g., universal primer sites) and/or one or more sequencing oligonucleotides for use in subsequent cluster generation and/or sequencing (e.g., known P5 and P7 sequences for used in sequencing by synthesis (SBS) (Illumina, San Diego, Calif.)).

At step 420, unligated or nicked dsDNA adapter-molecule constructs are labeled for subsequent removal or depletion from the sample. For example, in one embodiment, dsDNA adapter-molecule constructs containing a failed adapter ligation event and/or an unrepaired gap/nick site can be labeled with one or more labeled dNTP (e.g., biotin-dUTP) using a nick translation reaction. The nick translation reaction utilizes the free 3'-end of the unligated adapter, or the 3'-end of the dsDNA molecule, in an extension reaction to incorporate the one or more labeled dNTPs. In another embodiment, a primer extension reaction can be used to label the dsDNA adapter-molecule constructs containing a failed adapter ligation event and/or an unrepaired gap/nick site can be labeled with a labeled dNTP (e.g., biotin-dUTP). For example, a primer can be annealed to the ligated strand of a dsDNA adapter-molecule construct, and extended in a polymerization reaction incorporating the one or more labeled dNTPs (e.g., biotin-dUTP). As described above, a primer having a free 3'-OH is used in the primer extension reaction. The primer sequence can comprise a short oligonucleotide sequence having a length of from about 2 nt to about 50 nt, from about 2 nt to about 40 nt, from about 2 to about 30 nt, from about 2 to about 20 nt, or from about 2 to about 10 nt. In another embodiment, the primer sequence can comprise a short oligonucleotide sequence greater than about 2, 3, 4, 5, 6, 7, 8, 9, or 10 nucleotides (nt) in length.

At step 425, a pull-down protocol is performed to remove (or deplete) labeled adapter-molecule constructs. For example, as described above, a reaction mixture including one or more biotin-labeled dNTP can be used to label unligated or nicked dsDNA adapter-molecule constructs obtained from step 415. The biotin-labeled adapter-molecule constructs can then be removed (or depleted) from the sample using a streptavidin pull-down protocol. For example, the biotin label may be used for immobilization or isolation of the adapter-molecule constructs using a streptavidin-coated surface (e.g., streptavidin-coated beads). Immobilization of biotinylated molecules onto streptavidin capture beads can be used to capture and deplete the adapter-molecule constructs from the test sample. The streptavidin pull-down protocol immobilizes or removes the biotin-dNTP labeled adapter-molecule constructs allowing the fully ligated adapter-construct to remain in the test sample. In accordance with some embodiments of the present invention, the labeled dsDNA adapter-molecule constructs comprising a biotin-labeled strand and the corresponding complementary strand of the duplex DNA are removed (or depleted) from the sample.

At step 430, the remaining dsDNA adapter-molecule constructs (i.e., unlabeled adapter-molecule constructs) in the sample are amplified to generate a sequencing library. For example, the adapter-molecule constructs can be amplified by PCR using a DNA polymerase and a reaction mixture containing one or more primers and a mixture of dNTPs (i.e., dATP, dCTP, dGTP, and dTTP). As unligated or nicked adapter-molecule constructs are removed (depleted) in step 425, only fully ligated adapter-molecule constructs remain in the test sample.

At step 435 at least a portion of the sequencing library prepared in step 425 is sequenced to obtain sequencing data or sequence reads. In general, any method known in the art can be used to obtain sequence data or sequence reads from the sequencing library. For example, in one embodiment, sequencing data or sequence reads from the sequencing library can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences), sequencing by ligation (SOLiD sequencing), and nanopore sequencing (Oxford Nanopore Technologies). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step can be performed prior to sequencing. In accordance with the present invention, amplification of the adapter-molecule constructs remaining after depletion step 425 generates a plurality of double-stranded DNA (dsDNA) or duplex molecules comprising the forward (+ strand) and reverse (− strand) complement strands from the original dsDNA molecules. These dsDNA molecule constructs (i.e., containing both the forward strand and reverse complement strand) allow for subsequent sequencing of both the forward and reverse complement strands.

As shown in FIG. 4, at step 440, sequencing data or sequence reads are grouped into families based on their unique molecular identifiers (UMIs). As used herein, a "family group" comprises a plurality of sequence reads identified, based on their associated UMIs, as originating from a single double-strand DNA (dsDNA) molecule from the test sample. A "family" of sequence reads, as used herein, includes both a set of sequence reads originating from a specific forward (+) strand sequence and a set of sequence reads originating from the reverse (−) complement strand sequence (i.e., the forward strand and reverse complement from a single dsDNA molecule). For example, a family of sequence reads can be placed into a family group, where each of the sequence reads has either the same UMI (e.g., on a set of forward strands), or the reverse complement of the UMI sequence (e.g., on a set of reverse complement strands).

At step 445, the sequence reads within a family are compared to generate a consensus sequence for each family, thereby correcting sequencing derived errors in sequence reads. For example, the nucleotide base sequence for each of the plurality of sequence reads in a family (originating from both the forward strands and reverse complement strands) can be compared to determine the most probable nucleotide base at each position along the sequence. As used herein, a "consensus sequence" comprises a sequence of nucleotide bases identified as the most probable at each position along the sequence. In one embodiment, the consensus sequence comprises a sequence of nucleotide bases, wherein each base is identified as the most probable nucleotide base at a given position when a specific base is present at the position in a majority of the sequence reads within a family (i.e., from a plurality of sequence reads derived from both the forward and reverse complement strands within a family). In other embodiments, the consensus sequence comprises a sequence of nucleotide bases, wherein each base is identified as the most probable nucleotide base at a given position when a specific base is present at the position in at least 60%, at least 70%, at least 80%, at least 90%, or at least 95%, of the family members. In accordance with one embodiment, errors introduced during sample preparation and sequencing can be identified, and eliminated through the generation of a consensus sequence.

Figure 5:
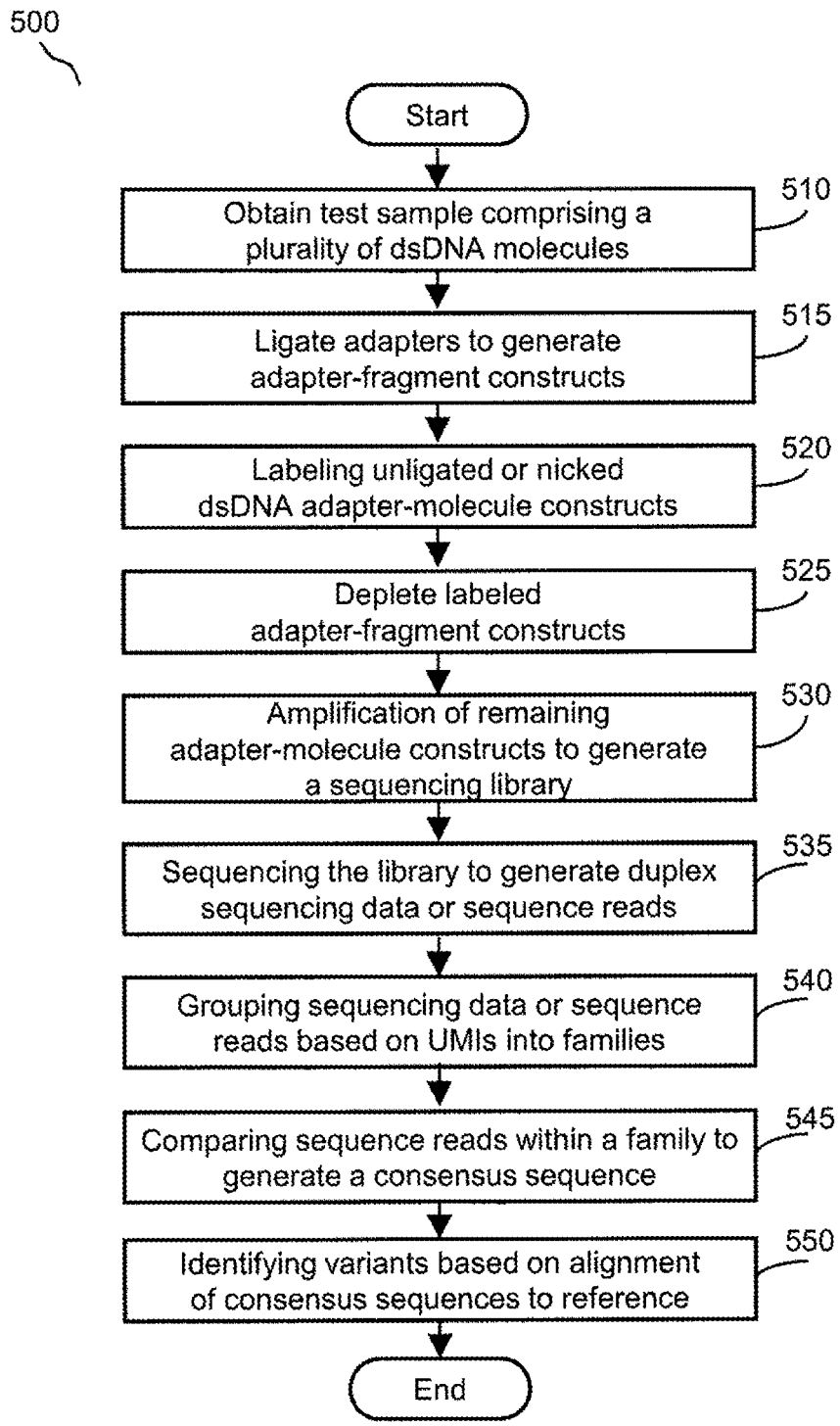
FIG. 5 is a flow diagram illustrating a method for variant detection, using a sequencing library prepared in accordance with the method of FIG. 1.

FIG. 5 is a flow diagram illustrating a method 500 for preparing an improved sequencing library for duplex sequencing based rare variant detection.

As shown in FIG. 5, at step 510, a biological test sample comprising a plurality of double-stranded DNA (dsDNA) molecules is obtained from a subject (e.g., a patient known to have or suspected of having cancer). As discussed in more detail elsewhere herein, the biological sample can be a blood, plasma, serum, urine, saliva samples, or any combination thereof. Alternatively, as noted above, the biological sample can be a whole blood, a blood fraction, a tissue biopsy, a pleural fluid, pericardial fluid, a cerebral spinal fluid, a peritoneal fluid, or any combination thereof. In accordance with some embodiments, the biological test sample can comprise a plurality of cell-free nucleic acids (e.g., cell-free DNA (cfDNA)) fragments. In some embodiments, the sample is a plasma sample from a cancer patient, or a patient suspected of having cancer. Optionally, the cell-free nucleic acids (e.g., cfDNA) can be extracted and/or purified from the biological test sample using any means known in the art.

Optionally, the double-stranded DNA (dsDNA) molecules are modified for adapter ligation. For example, the ends of dsDNA molecules are repaired using, for example, T4 DNA polymerase and/or Klenow polymerase and phosphorylated with a polynucleotide kinase enzyme prior to ligation of the adapters. A single "A" deoxynucleotide is then added to the 3' ends of dsDNA molecules using, for example, Taq polymerase enzyme, producing a single base 3' overhang that is complementary to a 3' base (e.g., a T) overhang on the dsDNA adapter.

At step 515, double-stranded DNA (dsDNA) adapters are ligated to both ends of the dsDNA molecules to generate adapter-molecule constructs. The ligation reaction can be performed using any suitable ligation step (e.g., using a ligase) which joins the dsDNA adapters to the dsDNA molecules to form circular adapter-dsDNA-adapter constructs. In one embodiment, the ligation reaction is performed using T4 DNA ligase. In another embodiment, T7 DNA ligase is used for adapter ligation to the dsDNA molecules. As described elsewhere herein, the adapters can comprise a unique molecular identifier (UMI). Furthermore, as noted elsewhere in this disclosure, the adapters can also include one or more primer binding sites (e.g., universal primer sites) and/or one or more sequencing oligonucleotides for use in subsequent cluster generation and/or sequencing (e.g., known P5 and P7 sequences for used in sequencing by synthesis (SBS) (Illumina, San Diego, Calif.)).

At step 520, unligated or nicked dsDNA adapter-molecule constructs are labeled for subsequent removal or depletion from the sample. For example, in one embodiment, dsDNA adapter-molecule constructs containing a failed adapter ligation event and/or an unrepaired gap/nick site can be labeled with one or more labeled dNTP (e.g., biotin-dUTP) using a nick translation reaction. The nick translation reaction utilizes the free 3'-end of the unligated adapter, or the 3'-end of the dsDNA molecule, in extension reaction to incorporate the one or more labeled dNTPs. In another embodiment, a primer extension reaction can be used to label the dsDNA adapter-molecule constructs containing a failed adapter ligation event and/or an unrepaired gap/nick site can be labeled with a labeled dNTP (e.g., biotin-dUTP). For example, a primer can be annealed to the ligated strand of a dsDNA adapter-molecule construct, and extended in a polymerization reaction incorporating the one or more labeled dNTPs (e.g., biotin-dUTP).

At step 525, a pull-down protocol is performed to remove (or deplete) labeled adapter-molecule constructs. For example, as described above, a reaction mixture including one or more biotin-labeled dNTP can be used to label unligated or nicked dsDNA adapter-molecule constructs obtained from step 515. The biotin-labeled adapter-molecule constructs can then be removed (or depleted) from the sample using a streptavidin pull-down protocol. For example, the biotin label may be used for immobilization or isolation of the adapter-molecule constructs using a streptavidin-coated surface (e.g., streptavidin-coated beads). Immobilization of biotinylated molecules onto streptavidin capture beads can be used to capture and deplete the adapter-molecule constructs from the test sample. The streptavidin pull-down protocol immobilizes or removes the biotin-dNTP labeled adapter-molecule constructs allowing the fully ligated adapter-molecule constructs to remain in the test sample. As described elsewhere herein, in some embodiments, the labeled dsDNA adapter-molecule constructs comprising a biotin-labeled strand and the corresponding complementary strand of the duplex DNA are removed (or depleted) from the sample.

At step 530, the remaining dsDNA adapter-molecule constructs (i.e., unlabeled adapter-molecule constructs) in the sample are amplified to generate a sequencing library. For example, the adapter-molecule constructs can be amplified by PCR using a DNA polymerase and a reaction mixture containing one or more primers and a mixture of dNTPs (i.e., dATP, dCTP, dGTP, and dTTP). As unligated or nicked adapter-molecule constructs are removed (depleted) in step 525, only fully ligated adapter-molecule constructs remain in the test sample.

At step 535, at least a portion of the sequencing library prepared in step 530 is sequenced to obtain sequencing data or sequence reads. In general, any method known in the art can be used to obtain sequence data or sequence reads from the sequencing library. For example, in one embodiment, sequencing data or sequence reads from the sequencing library can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences), sequencing by ligation (SOLiD sequencing), and nanopore sequencing (Oxford Nanopore Technologies). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step can be performed prior to sequencing. In accordance with the present invention, amplification of the adapter-molecule constructs remaining after step 525 generates a plurality of double-stranded DNA (ssDNA) molecules comprising the forward (+ strand) and reverse (− strand) complement strands from the original dsDNA molecules. These dsDNA molecule constructs (i.e., containing both the forward strand and reverse complement strand) allow for subsequent sequencing of both the forward and reverse complement strands.

As shown in FIG. 5, at step 540, sequencing data or sequence reads are grouped into families based on their unique molecular identifiers (UMIs). As used herein, a "family group" comprises a plurality of sequence reads identified, based on their associated UMIs, as originating from a single double-strand DNA (dsDNA) molecule from the test sample. A "family" of sequence reads, as used herein, includes both a set of sequence reads originating from a specific forward (+) strand sequence and a set of sequence reads originating from the reverse (−) complement strand sequence (i.e., the forward strand and reverse complement from a single dsDNA molecule). For example, a family of sequence reads can be placed into a family group, where each of the sequence reads has either the same UMI (e.g., on a set of forward strands), or the reverse complement of the UMI sequence (e.g., on a set of reverse complement strands).

At step 545, the sequence reads within a family are compared to generate a consensus sequence. For example, the nucleotide base sequence for each of the plurality of sequence reads in a family (originating from both the forward strands and reverse complement strands) can be compared to determine the most probable nucleotide base at each position along the sequence. As used herein, a "consensus sequence" comprises a sequence of nucleotide bases identified as the most probable at each position along the sequence. In one embodiment, the consensus sequence comprises a sequence of nucleotide bases, wherein each base is identified as the most probable nucleotide base at a given position when a specific base is present at the position in a majority of the sequence reads within a family (i.e., from a plurality of sequence reads derived from both the forward and reverse complement strands within a family). In other embodiments, the consensus sequence comprises a sequence of nucleotide bases, wherein each base is identified as the most probable nucleotide base at a given position when a specific base is present at the position in at least 60%, at least 70%, at least 80%, at least 90%, or at least 95%, of the family members. In accordance with one embodiment, errors introduced during sample preparation and sequencing can be identified, and eliminated through the generation of a consensus sequence.

Finally, as shown at step 550, the consensus sequence can be compared to, or aligned to, a reference sequence to identify a rare variant or mutation. For example, a rare variant or mutation can be identified where the consensus sequence varies at one or more nucleotide base positions compared to the reference sequence. Rare variants and/or mutations may include, for example, genetic alterations such as a somatic point mutation(s) (e.g., single nucleotide variations (SNVs)), somatic indels, and/or a somatic copy number alteration(s) (SCNA; e.g., amplification(s) and/or deletion(s)). In some embodiments, the somatic point mutation(s) (e.g., single nucleotide variations (SNVs)), somatic indels, and/or a somatic copy number alteration(s) (SCNA; e.g., amplification(s) and/or deletion(s)) may be tumor-derived. In accordance with one embodiment of the present invention, one or more rare variants and/or mutations identified herein can be used for detecting the presence or absence of cancer, determining cancer stage, monitoring cancer progression, and/or for determining a cancer classification (e.g., cancer type or cancer tissue of origin). In another embodiment, the sequencing data or sequence reads can be used to infer the presence or absence of cancer, cancer status and/or a cancer classification.

In one embodiment, one or more rare variants and/or mutations can be analyzed to detect the presence or absence of, determine the stage of, monitor progression of, and/or classify a cancer (including, but not limited to, a carcinoma, a sarcoma, a myeloma, a leukemia, a lymphoma, a blastoma, a germ cell tumor, or any combination thereof). In some embodiments, a carcinoma may be an adenocarcinoma. In other embodiments, the carcinoma may be a squamous cell carcinoma. In still other embodiments, the carcinoma is selected from the group consisting of: small cell lung cancer, non-small-cell lung, nasopharyngeal, colorectal, anal, liver, urinary bladder, cervical, testicular, ovarian, gastric, esophageal, head-and-neck, pancreatic, prostate, renal, thyroid, melanoma, and breast carcinoma. In another embodiment, one or more rare variants and/or mutations can be analyzed to detect presence or absence of, determine the stage of, monitor progression of, and/or classify a sarcoma. In certain embodiments, the sarcoma can be selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma. In still another embodiment, the one or more rare variants and/or mutations can be analyzed to detect the presence or absence of, determine the stage of, monitor progression of, and/or classify leukemia. In certain embodiments, the leukemia can be selected from the group consisting of: myelogenous, granulocytic, lymphatic, lymphocytic, and lymphoblastic leukemia. In still another embodiment, the one or more rare variants and/or mutations can be used to detect presence or absence of, determine the stage of, monitor progression of, and/or classify a lymphoma. In certain embodiments, the lymphoma can be selected from the group consisting of: Hodgkin's lymphoma and Non-Hodgkin's lymphoma.

Sequencing and Bioinformatics

As reviewed above, aspects of the invention include sequencing of nucleic acid molecules to generate a plurality of sequence reads, compilation of a plurality of sequence reads into a sequencing library, and bioinformatic manipulation of the sequence reads and/or sequencing library to determine sequence information from a test sample (e.g., a biological sample). In some embodiments, one or more aspects of the subject methods are conducted using a suitably-programmed computer system, as described further herein.

In certain embodiments, a sample is collected from a subject, followed by enrichment for genetic regions or genetic fragments of interest. For example, in some embodiments, a sample can be enriched by hybridization to a nucleotide array comprising cancer-related genes or gene fragments of interest. In some embodiments, a sample can be enriched for genes of interest (e.g., cancer-associated genes) using other methods known in the art, such as hybrid capture. See, e.g., Lapidus (U.S. Pat. No. 7,666,593), the contents of which is incorporated by reference herein in its entirety. In one hybrid capture method, a solution-based hybridization method is used that includes the use of biotinylated oligonucleotides and streptavidin coated magnetic beads. See, e.g., Duncavage et al., J Mol Diagn. 13(3): 325-333 (2011); and Newman et al., Nat Med. 20(5): 548-554 (2014). Isolation of nucleic acid from a sample in accordance with the methods of the invention can be done according to any method known in the art.

Sequencing may be by any method or combination of methods known in the art. For example, known DNA sequencing techniques include, but are not limited to, classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, Polony sequencing, and SOLiD sequencing. Sequencing of separated molecules has more recently been demonstrated by sequential or single extension reactions using polymerases or ligases as well as by single or sequential differential hybridizations with libraries of probes.

One conventional method to perform sequencing is by chain termination and gel separation, as described by Sanger et al., Proc Natl. Acad. Sci. USA, 74(12): 5463 67 (1977), the contents of which are incorporated by reference herein in their entirety. Another conventional sequencing method involves chemical degradation of nucleic acid fragments. See, Maxam et al., Proc. Natl. Acad. Sci., 74: 560 564 (1977), the contents of which are incorporated by reference herein in their entirety. Methods have also been developed based upon sequencing by hybridization. See, e.g., Harris et al., (U.S. patent application number 2009/0156412), the contents of which are incorporated by reference herein in their entirety.

A sequencing technique that can be used in the methods of the provided invention includes, for example, Helicos True Single Molecule Sequencing (tSMS) (Harris T. D. et al. (2008) Science 320:106-109), the contents of which are incorporated by reference herein in their entirety. Further description of tSMS is shown, for example, in Lapidus et al. (U.S. Pat. No. 7,169,560), the contents of which are incorporated by reference herein in their entirety, Lapidus et al. (U.S. patent application publication number 2009/0191565, the contents of which are incorporated by reference herein in their entirety), Quake et al. (U.S. Pat. No. 6,818,395, the contents of which are incorporated by reference herein in their entirety), Harris (U.S. Pat. No. 7,282,337, the contents of which are incorporated by reference herein in their entirety), Quake et al. (U.S. patent application publication number 2002/0164629, the contents of which are incorporated by reference herein in their entirety), and Braslaysky, et al., PNAS (USA), 100: 3960-3964 (2003), the contents of which are incorporated by reference herein in their entirety.

Another example of a DNA sequencing technique that can be used in the methods of the provided invention is 454 sequencing (Roche) (Margulies, M et al. 2005, Nature, 437, 376-380, the contents of which are incorporated by reference herein in their entirety). Another example of a DNA sequencing technique that can be used in the methods of the provided invention is SOLiD technology (Applied Biosystems). Another example of a DNA sequencing technique that can be used in the methods of the provided invention is Ion Torrent sequencing (U.S. patent application publication numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the contents of each of which are incorporated by reference herein in their entirety).

In some embodiments, the sequencing technology is Illumina sequencing. Illumina sequencing is based on the amplification of DNA on a solid surface using fold-back PCR and anchored primers. Genomic DNA can be fragmented, or in the case of cfDNA, fragmentation is not needed due to the already short fragments. Adapters are ligated to the 5'- and 3'-ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. Yet another example of a sequencing technique that can be used in the methods of the provided invention is nanopore sequencing (Soni G V and Meller A. (2007) Clin Chem 53: 1996-2001, the contents of which are incorporated by reference herein in their entirety). Another example of a sequencing technique that can be used in the methods of the provided invention involves using a chemical-sensitive field effect transistor (chemFET) array to sequence DNA (for example, as described in US Patent Application Publication No. 20090026082, the contents of which are incorporated by reference herein in their entirety). Another example of a sequencing technique that can be used in the methods of the provided invention involves using an electron microscope (Moudrianakis E. N. and Beer M. Proc Natl Acad Sci USA. 1965 March; 53:564-71, the contents of which are incorporated by reference herein in their entirety).

If the nucleic acid from the sample is degraded or only a minimal amount of nucleic acid can be obtained from the sample, PCR can be performed on the nucleic acid in order to obtain a sufficient amount of nucleic acid for sequencing (See, e.g., Mullis et al. U.S. Pat. No. 4,683,195, the contents of which are incorporated by reference herein in its entirety).

Biological Samples

Aspects of the invention involve obtaining a test sample, e.g., a biological sample, such as a tissue and/or body fluid sample, from a subject for purposes of analyzing a plurality of nucleic acids (e.g., a plurality of RNA molecules) therein. Samples in accordance with embodiments of the invention can be collected in any clinically-acceptable manner. Any test sample suspected of containing a plurality of nucleic acids can be used in conjunction with the methods of the present invention. In some embodiments, a test sample can comprise a tissue, a body fluid, or a combination thereof. In some embodiments, a biological sample is collected from a healthy subject. In some embodiments, a biological sample is collected from a subject who is known to have a particular disease or disorder (e.g., a particular cancer or tumor). In some embodiments, a biological sample is collected from a subject who is suspected of having a particular disease or disorder.

As used herein, the term "tissue" refers to a mass of connected cells and/or extracellular matrix material(s). Non-limiting examples of tissues that are commonly used in conjunction with the present methods include skin, hair, finger nails, endometrial tissue, nasal passage tissue, central nervous system (CNS) tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or non-human mammal. Tissue samples in accordance with embodiments of the invention can be prepared and provided in the form of any tissue sample types known in the art, such as, for example and without limitation, formalin-fixed paraffin-embedded (FFPE), fresh, and fresh frozen (FF) tissue samples.

As used herein, the term "body fluid" refers to a liquid material derived from a subject, e.g., a human or non-human mammal. Non-limiting examples of body fluids that are commonly used in conjunction with the present methods include mucous, blood, plasma, serum, serum derivatives, synovial fluid, lymphatic fluid, bile, phlegm, saliva, sweat, tears, sputum, amniotic fluid, menstrual fluid, vaginal fluid, semen, urine, cerebrospinal fluid (CSF), such as lumbar or ventricular CSF, gastric fluid, a liquid sample comprising one or more material(s) derived from a nasal, throat, or buccal swab, a liquid sample comprising one or more materials derived from a lavage procedure, such as a peritoneal, gastric, thoracic, or ductal lavage procedure, and the like.

In some embodiments, a test sample can comprise a fine needle aspirate or biopsied tissue. In some embodiments, a test sample can comprise media containing cells or biological material. In some embodiments, a test sample can comprise a blood clot, for example, a blood clot that has been obtained from whole blood after the serum has been removed. In some embodiments, a test sample can comprise stool. In one preferred embodiment, a test sample is drawn whole blood. In one aspect, only a portion of a whole blood sample is used, such as plasma, red blood cells, white blood cells, and platelets. In some embodiments, a test sample is separated into two or more component parts in conjunction with the present methods. For example, in some embodiments, a whole blood sample is separated into plasma, red blood cell, white blood cell, and platelet components.

In some embodiments, a test sample includes a plurality of nucleic acids not only from the subject from which the test sample was taken, but also from one or more other organisms, such as viral DNA/RNA that is present within the subject at the time of sampling.

Nucleic acid can be extracted from a test sample according to any suitable methods known in the art, and the extracted nucleic acid can be utilized in conjunction with the methods described herein. See, e.g., Maniatis, et al., Molecular Cloning: A Laboratory Manual, Cold Spring Harbor, N.Y., pp. 280-281, 1982, the contents of which are incorporated by reference herein in their entirety.

In one preferred embodiment, cell free nucleic acid (e.g., cell-free DNA (cfDNA) and/or cell-free RNA (cfRNA)) are extracted from a test sample. cfDNA are short base nuclear-derived DNA fragments present in several bodily fluids (e.g. plasma, stool, urine). See, e.g., Mouliere and Rosenfeld, PNAS 112(11): 3178-3179 (March 2015); Jiang et al., PNAS (March 2015); and Mouliere et al., Mol Oncol, 8(5):927-41 (2014). Tumor-derived circulating tumor nucleic acids (e.g., ctDNA and/or ctRNA) constitutes a minority population of cfNAs (i.e., cfDNA and/or cfRNA), in some cases, varying up to about 50%. In some embodiments, ctDNA and/or ctRNA varies depending on tumor stage and tumor type. In some embodiments, ctDNA and/or ctRNA varies from about 0.001% up to about 30%, such as about 0.01% up to about 20%, such as about 0.01% up to about 10%. The covariates of ctDNA and/or ctRNA are not fully understood, but appear to be positively correlated with tumor type, tumor size, and tumor stage. E.g., Bettegowda et al, Sci Trans Med, 2014; Newmann et al, Nat Med, 2014. Despite the challenges associated with the low population of ctDNA/ctRNA in cfNAs, tumor variants have been identified in ctDNA and/or ctRNA across a wide span of cancers. E.g., Bettegowda et al, Sci Trans Med, 2014. Furthermore, analysis of cfDNA and/or cfRNA versus tumor biopsy is less invasive, and methods for analyzing, such as sequencing, enable the identification of sub-clonal heterogeneity. Analysis of cfDNA and/or cfRNA has also been shown to provide for more uniform genome-wide sequencing coverage as compared to tumor tissue biopsies. In some embodiments, a plurality of cfDNA and/or cfRNA are extracted from a sample in a manner that reduces or eliminates co-mingling of cfDNA and genomic DNA. For example, in some embodiments, a sample is processed to isolate a plurality of the cfDNA and/or cfRNA therein in less than about 2 hours, such as less than about 1.5, 1 or 0.5 hours.

A non-limiting example of a procedure for preparing nucleic acid from a blood sample follows. Blood may be collected in 10 mL EDTA tubes (for example, the BD VACUTAINER® family of products from Becton Dickinson, Franklin Lakes, N.J.), or in collection tubes that are adapted for isolation of cfDNA (for example, the CELL FREE DNA BCT® family of products from Streck, Inc., Omaha, Nebr.) can be used to minimize contamination through chemical fixation of nucleated cells, but little contamination from genomic DNA is observed when samples are processed within 2 hours or less, as is the case in some embodiments of the present methods. Beginning with a blood sample, plasma may be extracted by centrifugation, e.g., at 3000 rpm for 10 minutes at room temperature minus brake. Plasma may then be transferred to 1.5 ml tubes in 1 ml aliquots and centrifuged again at 7000 rpm for 10 minutes at room temperature. Supernatants can then be transferred to new 1.5 ml tubes. At this stage, samples can be stored at $-80°$ C. In certain embodiments, samples can be stored at the plasma stage for later processing, as plasma may be more stable than storing extracted cfDNA and/or cfRNA.

Plasma DNA and/or RNA can be extracted using any suitable technique. For example, in some embodiments, plasma DNA and/or RNA can be extracted using one or more commercially available assays, for example, the QIAmp Circulating Nucleic Acid Kit family of products (Qiagen N.V., Venlo Netherlands). In certain embodiments, the following modified elution strategy may be used. DNA and/or RNA may be extracted using, e.g., a QIAmp Circulating Nucleic Acid Kit, following the manufacturer's instructions (maximum amount of plasma allowed per column is 5 mL). If cfDNA and/or cfRNA are being extracted from plasma where the blood was collected in Streck tubes, the reaction time with proteinase K may be doubled from 30 min to 60 min. Preferably, as large a volume as possible should be used (i.e., 5 mL). In various embodiments, a two-step elution may be used to maximize cfDNA and/or cfRNA yield. First, DNA and/or RNA can be eluted using 30 µL of buffer AVE for each column. A minimal amount of buffer necessary to completely cover the membrane can be used in the elution in order to increase cfDNA and/or cfRNA concentration. By decreasing dilution with a small amount of buffer, downstream desiccation of samples can be avoided to prevent melting of double stranded DNA or material loss. Subsequently, about 30 µL of buffer for each column can be eluted. In some embodiments, a second elution may be used to increase DNA and/or RNA yield.

In other embodiments, RNA can be extracted and/or isolated using any suitable technique. For example, in some embodiments, RNA can be extracted using a commercially-available kit and/or protocol, e.g., a QIAamp Circulating Nucleic Acids kit and micro RNA extraction protocol.

In some embodiments, the methods involve DNase treating an extracted nucleic acid sample to remove cell-free DNA from a mixed cfDNA and cfRNA test sample.

Computer Systems and Devices

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer programs include, by way of example, both general and special purpose microprocessors, and any one or more processors of any kind of digital computer. Generally, a processor will receive instructions and data from a read-only memory or a random access memory, or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including, by way of example, semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through a network by any form or medium of digital data communication, e.g., a communication network. For example, a reference set of data may be stored at a remote location and a computer can communicate across a network to access the reference data set for comparison purposes. In other embodiments, however, a reference data set can be stored locally within the computer, and the computer accesses the reference data set within the CPU for comparison purposes. Examples of communication networks include, but are not limited to, cell networks (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, a data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification (RFID) tags or chips, or any other medium that can be used to store the desired information, and which can be accessed by a computing device.

Functions described herein can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system for implementing some or all of the described inventive methods can include one or more processors (e.g., a central processing unit (CPU) a graphics processing unit (GPU), or both), main memory and static memory, which communicate with each other via a bus.

A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to, one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

Additionally, systems of the invention can be provided to include reference data. Any suitable genomic data may be stored for use within the system. Examples include, but are not limited to: comprehensive, multi-dimensional maps of the key genomic changes in major types and subtypes of cancer from The Cancer Genome Atlas (TCGA); a catalog of genomic abnormalities from The International Cancer Genome Consortium (ICGC); a catalog of somatic mutations in cancer from COSMIC; the latest builds of the human genome and other popular model organisms; up-to-date reference SNPs from dbSNP; gold standard indels from the 1000 Genomes Project and the Broad Institute; exome capture kit annotations from Illumina, Agilent, Nimblegen, and Ion Torrent; transcript annotations; small test data for experimenting with pipelines (e.g., for new users).

In some embodiments, data is made available within the context of a database included in a system. Any suitable database structure may be used including relational databases, object-oriented databases, and others. In some embodiments, reference data is stored in a relational database such as a "not-only SQL" (NoSQL) database. In certain embodiments, a graph database is included within systems of the invention. It is also to be understood that the term "database" as used herein is not limited to one single database; rather, multiple databases can be included in a system. For example, a database can include two, three, four, five, six, seven, eight, nine, ten, fifteen, twenty, or more individual databases, including any integer of databases therein, in accordance with embodiments of the invention. For example, one database can contain public reference data, a second database can contain test data from a patient, a third database can contain data from healthy individuals, and a fourth database can contain data from sick individuals with a known condition or disorder. It is to be understood that any other configuration of databases with respect to the data contained therein is also contemplated by the methods described herein.

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof. All references cited throughout the specification are expressly incorporated by reference herein.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the present invention. All such modifications are intended to be within the scope of the claims appended hereto.

EXAMPLES

Example 1: Library Preparation from Sheared Genomic DNA

To evaluate method 200 of FIG. 2, sheared gDNA (a mixture of NA24631 and NA12878 cell-line gDNA) was used as input material for library preparation and purified ligation products were resolved on a Fragment Analyzer to assess incorporation of the biotin-dUTP label. Incorporation of biotin-dUTP (step 235 of method 200) changes the mobility of fragments during capillary electrophoresis on the Fragment Analyzer.

Figure 6:
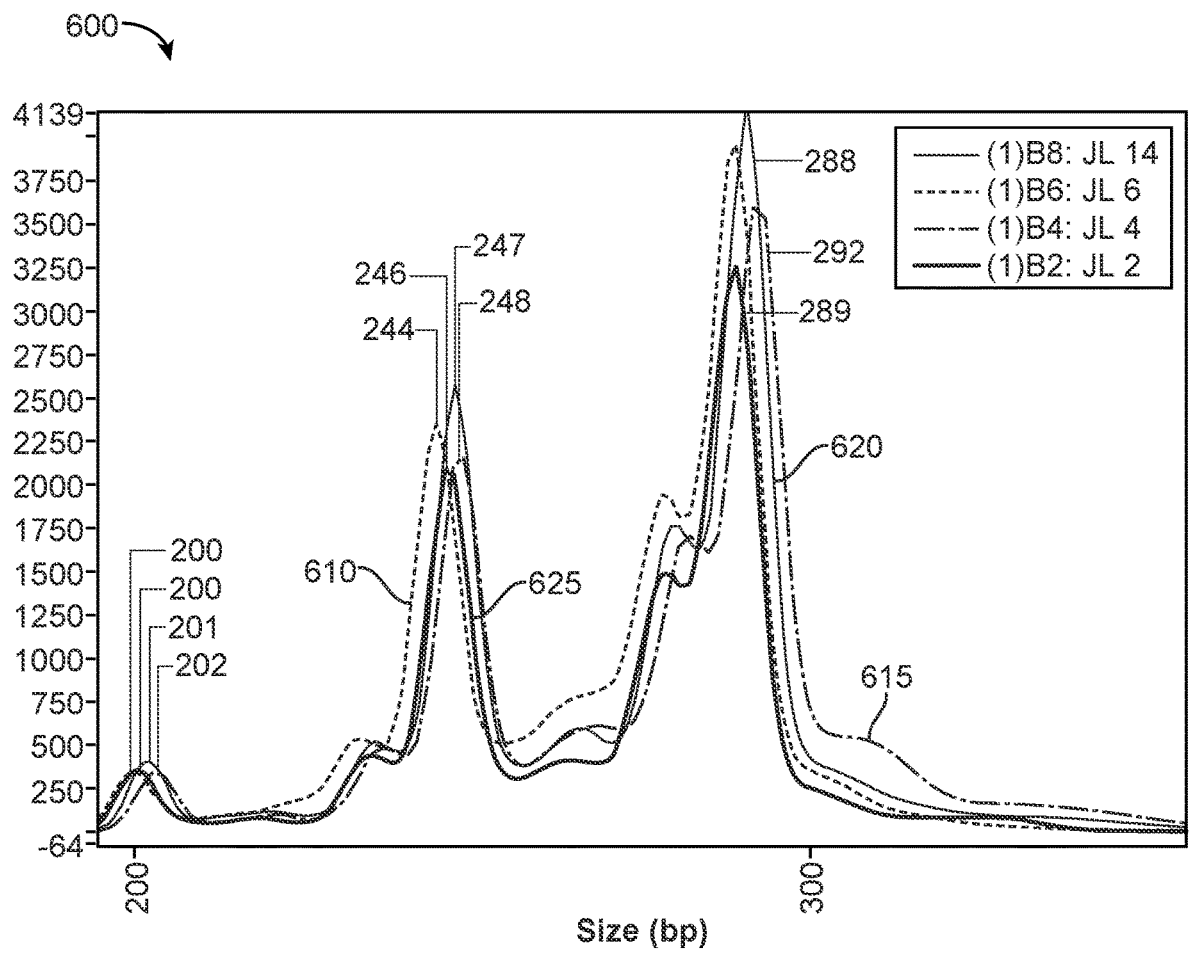
FIG. 6 is a plot of the fragment size distributions in four libraries prepared using the method of FIG. 2 and Klenow exo-DNA polymerase in a nick translation biotin-dUTP labeling reaction.

FIG. 6 is a plot 600 of the fragment size distributions in four libraries prepared using method 200 of FIG. 2 and Klenow exo-DNA polymerase in a nick translation biotin-dUTP labeling reaction (i.e., no extension primer/primer extension reaction). Plot 600 shows a first curve 610 (red line) of the fragment size distribution in a library (JL6) prepared without biotin-dUTP labeling (step 235) and streptavidin pull-down (step 240). The JL6 library sample served as an input control for the labeling and pull-down process. Three peaks were observed: a peak at about 200 bp that represents the fragment inserts with no ligated adapters; a peak at about 245 bp that represents the fragments with 1 adapter ligated; and a peak at about 290 bp that represents the fragment with two adapters ligated.

Plot 600 also shows a second curve 615 (blue line) of the fragment size distribution in a second library (JL4) prepared without streptavidin pull-down (step 240). The JL4 library sample illustrates a library profile after a fraction of the library has been labeled with biotin-dUTP but prior to depletion step 240. An increase in mass above 300 bp was observed, indicating that certain fragments in the library were successfully labeled.

Plot 600 also shows a third curve 620 (orange line) of the fragment size distribution in a third library (JL14) prepared essentially the same as the JL4 library (curve 615), except that a heat inactivation step was used after ligation of the adapters to dsDNA fragments (i.e., step 230). The JL14 library sample demonstrates that heat inactivation of the ligation products inhibits subsequent biotin-dUTP labeling (step 235).

Plot 600 also shows a fourth curve 625 (black line) of the fragment size distribution in a fourth library (JL2) prepared using method 200 as described with reference to FIG. 2. The JL2 library sample illustrates a library profile after the removal (or depletion) of library fragments containing biotin-dUTP. The data show that the peak above about 300 bp was removed and the peak heights at about 245 bp and about 290 bp were reduced, indicating successful removal of the biotin-dUTP labeled fragments.

Figure 7:
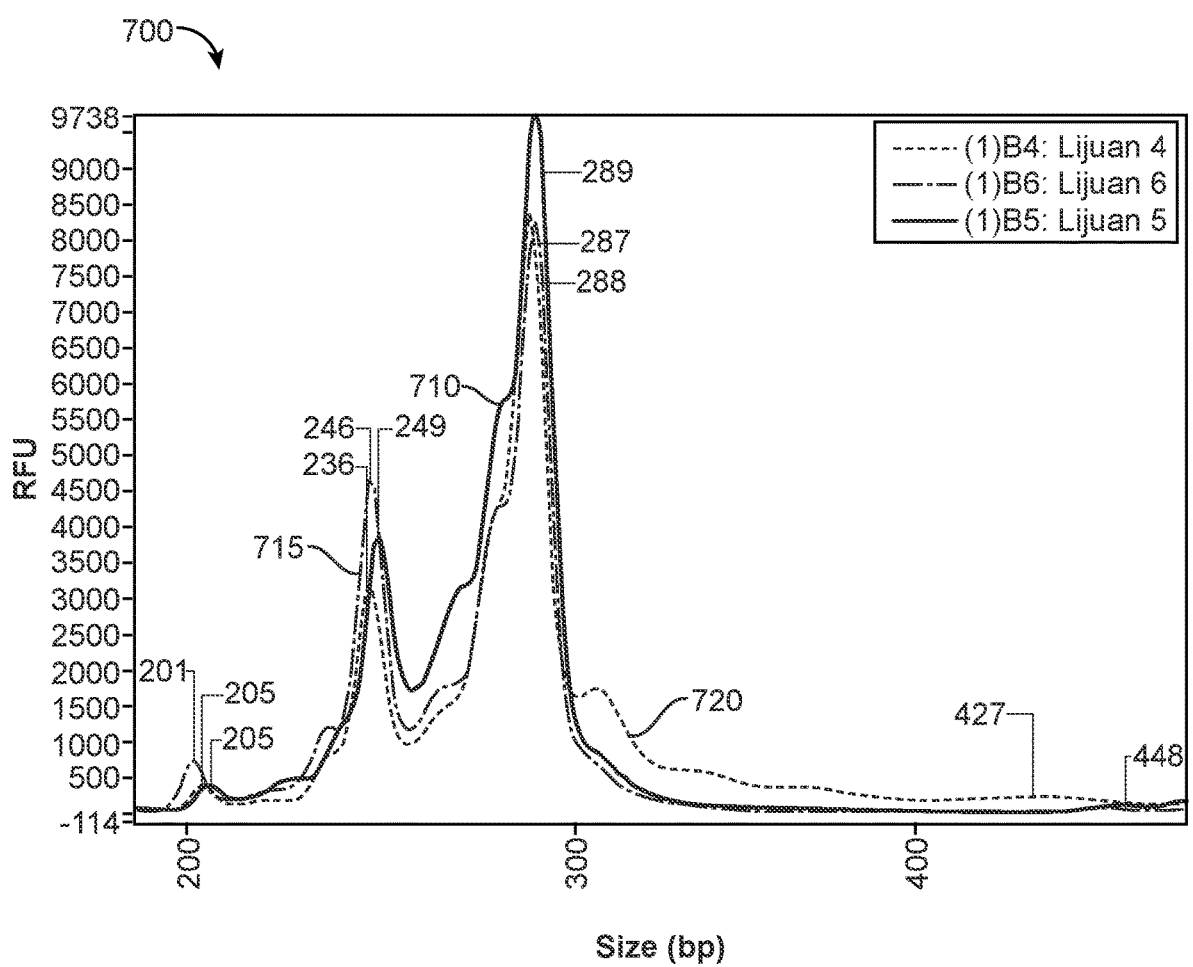
FIG. 7 is a plot of the fragment size distributions in three libraries prepared using the method of FIG. 2 and Bst 3.0 DNA polymerase in a nick translation biotin-dUTP labeling reaction.

FIG. 7 is a plot 700 of the fragment size distributions in three libraries prepared using method 200 of FIG. 2 and Bst 3.0 DNA polymerase in a nick translation biotin-dUTP labeling reaction (i.e., no extension primer/primer extension reaction). Plot 700 shows a first curve 710 (black line) of the fragment size distribution in a first library (L5) and a second curve 715 (blue line) of the fragment size distribution in a second library (L6) prepared without biotin-dUTP labeling (step 235) and streptavidin pull-down (step 240). The L5 and L6 library samples served as an input control for the labeling process. Three peaks were observed: a peak at about 200 bp that represents the fragment inserts with no ligated adapters; a peak at about 245 bp that represents the fragments with 1 adapter ligated; and a peak at about 290 bp that represents the fragment with two adapters ligated.

Plot 700 also shows a third curve 720 (red line) of the fragment size distribution in a third library (L4) prepared without streptavidin pull-down (step 240). The L4 library sample illustrates a library profile after a fraction of the library has been labeled with biotin-dUTP (i.e., pellet and supernatant fractions have not been separated). An increase in mass above 300 bp was observed, indicating that certain fragments in the library were successfully labeled.

Figure 8:
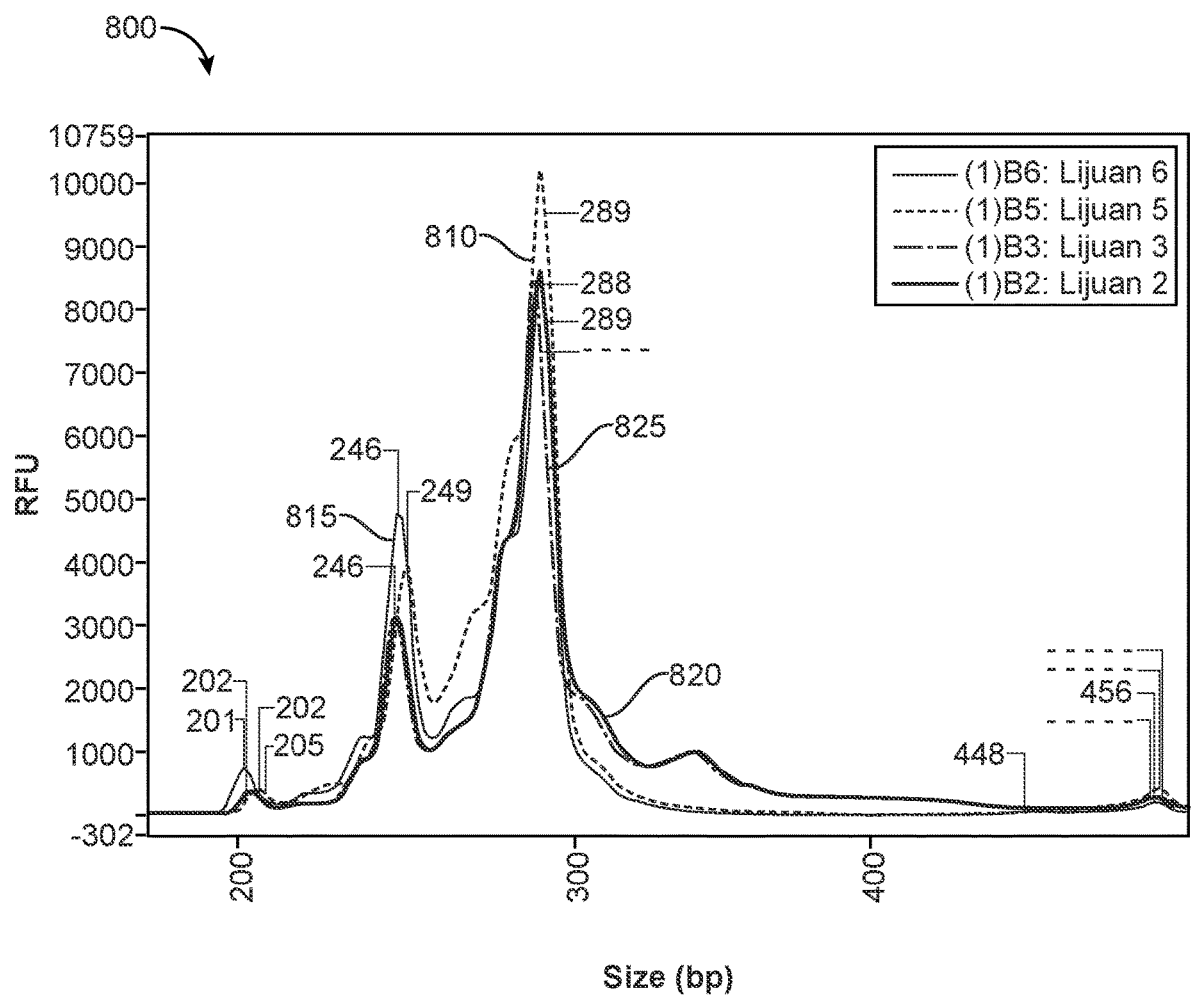
FIG. 8 is a plot of the fragment size distributions in four libraries prepared using the method of FIG. 2 and Klenow exo-DNA polymerase in a combined nick translation reaction/primer extension biotin-dUTP labeling reaction.

FIG. 8 is a plot 800 of the fragment size distributions in four libraries prepared using method 200 of FIG. 2 and Klenow exo-DNA polymerase in a combined nick translation reaction/primer extension biotin-dUTP labeling reaction (i.e., extension primer was added in the labeling reaction). Plot 800 shows a first curve 810 (red line) of the fragment size distribution in a first library (L5) and a second curve 815 (orange line) of the fragment size distribution in a second library (L6) prepared without biotin-dUTP labeling (step 235) and streptavidin pull-down (step 240). The L5 and L6 library samples served as an input control for the labeling process. Three peaks were observed: a peak at about 200 bp that represents the fragment inserts with no ligated adapters; a peak at about 245 bp that represents the fragments with 1 adapter ligated; and a peak at about 290 bp that represents the fragment with two adapters ligated.

Plot 800 also shows a third curve 820 (black line) of the fragment size distribution in a third library (L2) and a fourth curve 820 (blue line) of the fragment size distribution in a fourth library (L3) prepared without streptavidin pull-down (step 240). The L2 and L3 library samples illustrate library profiles after a fraction of the library has been labeled with biotin-dUTP (i.e., pellet and supernatant fractions have not been separated). An increase in mass above 300 bp was observed, indicating that certain fragments in the library were successfully labeled.

Example 2: Improved Recovery of Duplex DNA Using Klenow Exo–

Figure 9:
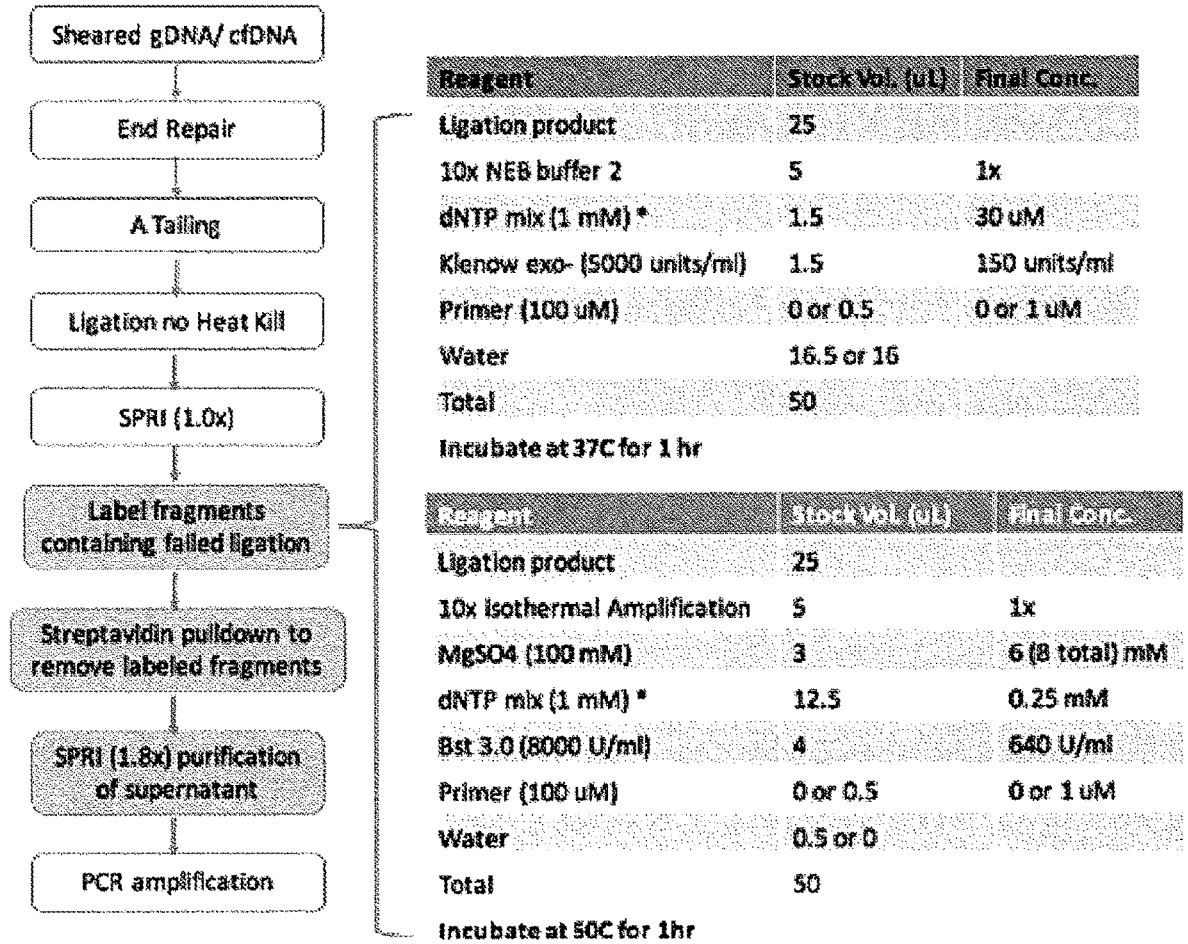
FIG. 9 is a flow chart showing an experimental procedure in accordance with some embodiments of the methods of present disclosure. Two different experimental conditions are depicted for the step that involves labeling of the DNA fragments that contain a failed adapter ligation event and/or an unrepaired gap/nick site.

The effect of a biotin labeling reaction and removal/depletion procedure on the percentage of duplex DNA recovery under different reaction conditions was evaluated using the workflow depicted in FIG. 9. Cell free DNA was used as the input material, and was subjected to end-repair, A-tailing, ligation using either a Klenow exo-polymerase or a Bst 3.0 polymerase, followed by an SPRI purification procedure. DNA fragments containing a failed adapter ligation event and/or an unrepaired gap/nick site were labeled with biotin using one of the two procedures outlined in FIG. 9.

Figure 10:
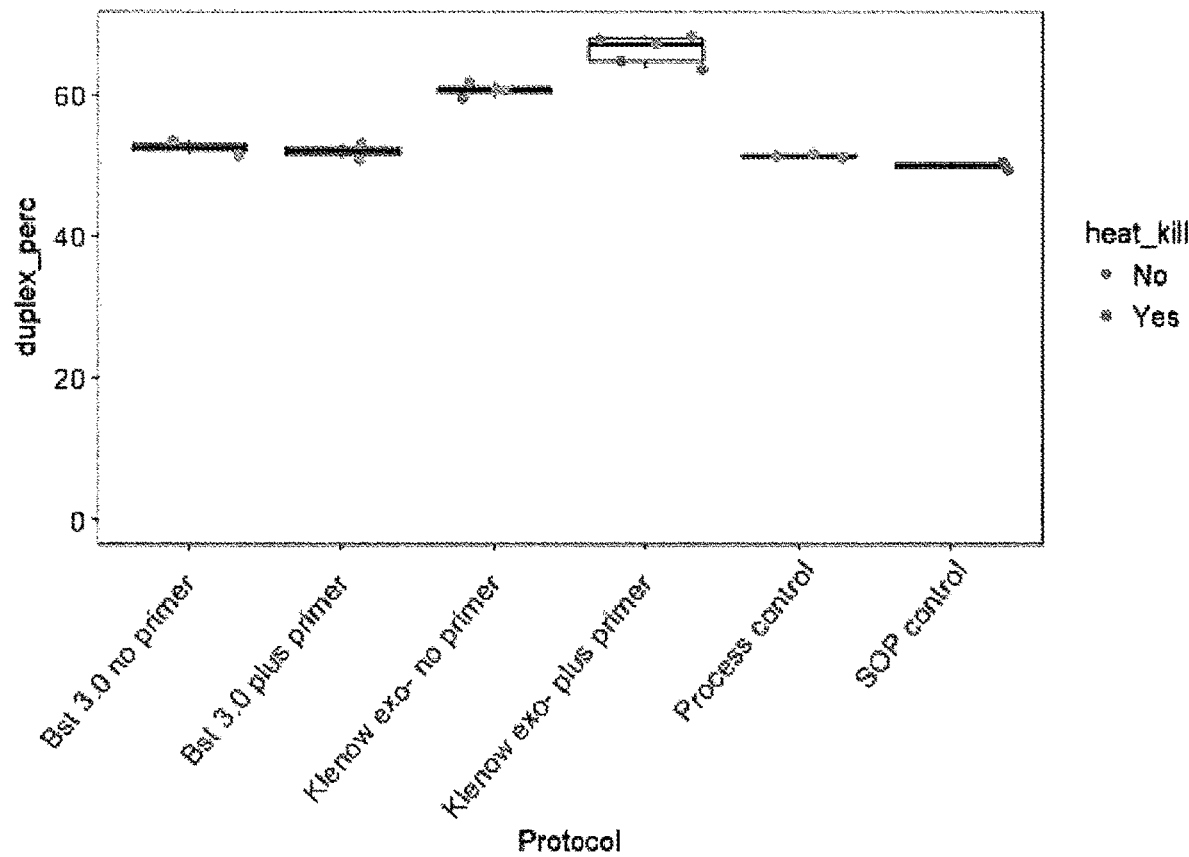
FIG. 10 is a graph showing the percentage of duplex DNA recovered from experiments using the reaction conditions depicted on the X-axis. The effects of an optional heat kill step are also depicted in the graph.

A streptavidin pull-down procedure was then used to remove (or deplete) the biotin-labeled DNA fragments, followed by another SPRI purification procedure. The purified DNA was then evaluated to determine the percentage of duplex DNA present. The results are provided in FIG. 10.

The results demonstrate that the choice of polymerase enzyme had an impact on the percentage of duplex DNA recovered from the reaction. Notably, the Bst 3.0 polymerase resulted in approximately 51.4% duplex DNA recovery, which was comparable to the process control and SOP control procedures (approximately 50.0%). The Klenow exo-polymerase enzyme, in contrast, resulted in approximately 61% duplex DNA recovery under the "no primer" conditions, and increased further to approximately 67.8% under the "plus primer" conditions. Additional improvements may be possible through refinement of the reaction conditions, as one of skill in the art would readily appreciate.

What is claimed is:

1. A method for preparing a sequencing library from a test sample comprising a plurality of double-stranded DNA molecules, the method comprising:
   (a) obtaining a test sample comprising a plurality of double-stranded DNA (dsDNA) molecules, wherein the dsDNA molecules comprise a forward strand sequence and a reverse complement strand sequence;
   (b) ligating dsDNA adapters to both ends of the dsDNA molecules, generating a plurality of dsDNA adapter-molecule constructs, wherein the dsDNA adapter comprises a unique molecular identifier (UMI);
   (c) incorporating one or more biotin-labeled nucleotides into partially ligated or nicked dsDNA adapter-molecule constructs to create a plurality of labeled dsDNA adapter-molecule constructs;
   (d) depleting the labeled dsDNA adapter-molecule constructs from the test sample; and
   (e) amplifying the remaining dsDNA adapter-molecule constructs in the depleted test sample to generate a sequencing library.

2. The method according to claim 1, further comprising:
   (f) sequencing at least a portion of the sequencing library to obtain a plurality of sequence reads;
   (g) grouping the sequence reads into families based on the UMIs, wherein each family comprises a first set of forward strand sequences each having a first UMI and a second set of reverse complement strand sequences each having a second UMI; and
   (h) comparing the sequence reads within each family to generate a consensus sequence for each family, thereby correcting sequencing-derived errors in sequence reads.

3. The method according to claim 2, further comprising:
   (i) aligning the consensus sequences to a reference sequence and identifying consensus sequences as one or more rare variants if the one or more consensus sequences vary from the reference sequence at one or more nucleotide positions.

4. The method according to claim 1, wherein the dsDNA molecules are cell-free DNA (cfDNA) molecules.

5. The method according to claim 4, wherein the cfDNA molecules originate from healthy cells and from cancer cells.

6. The method according to claim 1, wherein the plurality of dsDNA molecules are modified prior to adapter ligation, and wherein the modification comprises end-repairing and A-tailing prior to adapter ligation.

7. The method according to of claim 1, wherein the adapters further comprise a sample-specific index sequence.

8. The method according to claim 1, wherein the adapters further comprise a universal priming site.

9. The method according to claim 1, wherein the adapters further comprise one or more sequencing oligonucleotides for use in cluster generation and/or sequencing.

10. The method according to claim 1, wherein one or more biotin-labeled nucleotides are incorporated into partially ligated or nicked dsDNA adapter-molecule constructs using a DNA polymerase.

11. The method according to claim 10, wherein the DNA polymerase is a DNA polymerase comprising strand displacement activity.

12. The method according to claim 10, wherein the DNA polymerase lacks exonuclease activity.

13. The method according to claim 10, wherein the DNA polymerase is *Bacillus stearothermophilus* DNA polymerase (Bst Pol), a Klenow DNA polymerase, or a phi29 DNA polymerase.

14. The method according to claim 13, wherein the DNA polymerase is a Klenow DNA polymerase that lacks exonuclease activity.

15. The method according to claim 2, wherein the consensus sequence comprises a sequence of nucleotide bases, wherein each base is identified at a given position in the sequence when a specific base is present in a majority of the sequence reads of the family.

16. The method according to claim 2, wherein the method further comprises loading at least a portion of the sequence library into a sequencing flow cell and generating a plurality of sequencing clusters on the flow cell, wherein the clusters comprise the forward strand sequence and the reverse complement strand sequence.

17. The method according to claim 3, wherein the method further comprises using the one or more rare variants to detect the presence or absence of a cancer, determine a cancer status, monitor cancer progression, and/or determine a cancer classification.

18. The method according to claim 17, wherein monitoring cancer progression comprises monitoring disease progression, monitoring therapy, or monitoring cancer growth.

19. The method according to claim 17, wherein the cancer classification comprises determining a cancer type and/or a cancer tissue of origin.

20. The method according to claim 17, wherein the cancer comprises a carcinoma, a sarcoma, a myeloma, a leukemia, a lymphoma, a blastoma, a germ cell tumor, or any combination thereof.

* * * * *

UNITED STATES PATENT AND TRADEMARK OFFICE
CERTIFICATE OF CORRECTION

PATENT NO. : 11,414,656 B2
APPLICATION NO. : 16/221358
DATED : August 16, 2022
INVENTOR(S) : Lijuan Ji, Nathan Hunkapiller and Suchitra Ramani It is certified that error appears in the above-identified patent and that said Letters Patent is hereby corrected as shown below:

On the Title Page

Correct Applicant Name to read as GRAIL, LLC, Menlo Park, CA

Signed and Sealed this
Eighth Day of November, 2022

Katherine Kelly Vidal
*Director of the United States Patent and Trademark Office*